United States Patent
Zhang et al.

(10) Patent No.: US 8,513,013 B2
(45) Date of Patent: Aug. 20, 2013

(54) GENERATION OF NOVEL BONE FORMING CELLS (MONOOSTEOPHILS) FROM LL-37 TREATED MONOCYTES

(75) Inventors: Zhifang Zhang, Glendora, CA (US); John E. Shively, Arcadia, CA (US)

(73) Assignee: City of Hope, Duarte, CA (US)

( * ) Notice: Subject to any disclaimer, the term of this patent is extended or adjusted under 35 U.S.C. 154(b) by 0 days.

(21) Appl. No.: 13/249,877

(22) Filed: Sep. 30, 2011

(65) Prior Publication Data

US 2012/0177689 A1    Jul. 12, 2012

Related U.S. Application Data

(60) Provisional application No. 61/388,471, filed on Sep. 30, 2010.

(51) Int. Cl.
*C12N 5/02* (2006.01)
*C12N 5/077* (2010.01)
*C12N 5/0786* (2010.01)

(52) U.S. Cl.
USPC ............................. 435/377; 435/325; 435/372

(58) Field of Classification Search
None
See application file for complete search history.

(56) References Cited

FOREIGN PATENT DOCUMENTS

WO    WO 2010026489 A1 *    3/2010

OTHER PUBLICATIONS

Bowdish et al., Journal of Immunology Mar. 15, 2004 vol. 172(6): 3758-3765.*
Mookherjee et al., Journal of Immunology Aug. 15, 2009 vol. 183(4): 2688-2696.*
Van der Does et al., The Journal of Immunology Aug. 1, 2010 vol. 185(3): 1442-1449.*
Agerberth, B, Charo J, Werr J, Olsson B, Idali F, et al. The human antimicrobial and chemotactic peptides LL-37 and alpha-defensins are expressed by specific lymphocyte and monocyte populations. *Blood* 96:3086-3093 (2000).
Bandholtz, L., Ekman GJ, Vilhelmsson M, Buentke E, Agerberth B, et al. Antimicrobial peptide LL-37 internalized by immature human dendritic cells alters their phenotype. *Scand J Immunol* 63:410-419 (2006).
Davidson, D.J., Currie AJ, Reid GS, Bowdish DM, MacDonald KL, et al. The cationic antimicrobial peptide LL-37 modulates dendritic cell differentiation and dendritic cell-induced T cell polarization. *J Immunol* 172:1146-1156 (2004).
Davidson, D.J., Currie AJ, Reid GS, Bowdish DM, MacDonald KL, et al. The cationic antimicrobial peptide LL-37 modulates dendritic cell differentiation and dendritic cell-induced T cell polarization. Correction *J Immunol* 172:2704 (2004).
De, Y., Chen Q, Schmidt AP, Anderson GM, Wang JM, et al. LL-37, the neutrophil granule- and epithelial cell-derived cathelicidin, utilizes formyl peptide receptor-like 1 (FPRL1) as a receptor to chemoattract human peripheral blood neutrophils, monocytes, and T cells. *J Exp Med* 192:1069-1074 (2000).
Ducy, P., Schinke T, Karsenty G. The osteoblast: a sophisticated fibroblast under central surveillance. *Science* 289:1501-1504 (2000).
Falzoni, S., Munerati M, Ferrari D, Spisani S, Moretti S, et al. The purinergic P2Z receptor of human macrophage cells. Characterization and possible physiological role. *J Clin Invest* 95:1207-1216 (1995).
Fernandez, Pujol B., Lucibello FC, Gehling UM, Lindemann K, Weidner N, et al. Endothelial-like cells derived from human CD14 positive monocytes. *Differentiation* 65:287-300 (2000).
Franc, N.C., Dimarcq JL, Lagueux M, Hoffmann J, Ezekowitz RA. Croquemort, a novel Drosophila hemocyte/macrophage receptor that recognizes apoptotic cells. *Immunity* 4:431-443 (1996).
Frohm, M., Gunne H, Bergman AC, Agerberth B, Bergman T, et al. Biochemical and antibacterial analysis of human wound and blister fluid. *Eur J Biochem* 237:86-92 (1996).
Geissmann, F., Jung S, Littman DR. Blood monocytes consist of two principal subsets with distinct migratory properties. *Immunity* 19:71-82 (2003).
Gordon, S. The macrophage. *Bioessays* 17:977-986 (1995).
Hayman, AR, Bune AJ, Bradley JR, Rashbass J, Cox TM. Osteoclastic tartrateresistant acid phosphatase (Acp 5): its localization to dendritic cells and diverse murine tissues. *J Histochem Cytochem* 48:219-227 (2000).
Heilborn, J.D., Nilsson MF, Kratz G, Weber G, Sorensen O, et al. The cathelicidin anti-microbial peptide LL-37 is involved in re-epithelialization of human skin wounds and is lacking in chronic ulcer epithelium. *J Invest Dermatol* 120:379-389 (2003).
Isenmann, S., Arthur A, Zannettino AC, Turner JL, Shi S, et al. Twist family of basic helix-loop-helix transcription factors mediate human mesenchymal stem cell growth and commitment. *Stem Cells* 27:2457-2468 (2009).
Jilka, R.L., Weinstein RS, Bellido T, Parfitt AM, Manolagas SC. Osteoblast programmed cell death (apoptosis): modulation by growth factors and cytokines. *J Bone Miner Res* 13:793-802 (1998).

(Continued)

*Primary Examiner* — Daniel C Gamett
(74) *Attorney, Agent, or Firm* — Perkins Coie LLP

(57) ABSTRACT

In one embodiment, a monocyte derived bone-forming cell population is provided. In one embodiment, the cell population comprises an isolated monocyte cell population treated with an effective dose of LL-37. In another embodiment, a method of producing a population of monocyte-derived bone-forming cells is provided. The method comprises obtaining a blood sample from a subject; isolating a population of monocytes from the blood sample; treating the isolated monocytes with an effective dose of LL-37; and culturing the LL-37 treated monocytes until they differentiate into the population of monocyte-derived bone-forming cells. In another embodiment, a method of treatment for a bone injury or bone disease is provided. The method comprises administering a therapeutically effective amount of a composition to a subject having the bone injury or disease, the composition comprising a population of monoosteophils.

9 Claims, 22 Drawing Sheets

(56) References Cited

OTHER PUBLICATIONS

Johansson, J., Gudmundsson GH, Rottenberg ME, Berndt KD, Agerberth B. Conformation-dependent antibacterial activity of the naturally occurring human peptide LL-37. *J Biol Chem* 273:3718-3724 (1998).

Kake, T., Kitamura H, Adachi Y, Yoshioka T, Watanabe T, et al. Chronically elevated plasma C-type natriuretic peptide level stimulates skeletal growth in transgenic mice. *Am J Physiol Endocrinol Metab* 297:E1339-1348 (2009).

Kandler, K., Shaykhiev R, Kleemann P, Klescz F, Lohoff M, et al. The antimicrobial peptide LL-37 inhibits the activation of dendritic cells by TLR ligands. *Int Immunol* 18:1729-1736 (2006).

Khosla, S., Westendorf JJ, Oursler MJ. Building bone to reverse osteoporosis and repair fractures. *J Clin Invest* 118:421-428 (2008).

Koczulla, R., von Degenfeld G, Kupatt C, Krotz F, Zahler S, et al. An angiogenic role for the human peptide antibiotic LL-37/hCAP-18. *J Clin Invest* 111:1665-1672 (2003).

Kuwana, M., Okazaki Y, Kodama H, Izumi K, Yasuoka H, et al. Human circulating CD14+ monocytes as a source of progenitors that exhibit mesenchymal cell differentiation. *J Leukoc Biol* 74:833-845 (2003).

Lacey, D.L., Timms E, Tan HL, Kelley MJ, Dunstan CR, et al. Osteoprotegerin ligand is a cytokine that regulates osteoclast differentiation and activation. *Cell* 93:165-176 (1998).

Malm, J., Sorensen O, Persson T, Frohm-Nilsson M, Johansson B, et al. The human cationic antimicrobial protein (hCAP-18) is expressed in the epithelium of human epididymis, is present in seminal plasma at high concentrations, and is attached to spermatozoa. *Infect Immun* 68:4297-4302 (2000).

Manolagas, S.C. Birth and death of bone cells: basic regulatory mechanisms and implications for the pathogenesis and treatment of osteoporosis. *Endocr Rev* 21:115-137 (2000).

Miyamoto, T., Ohneda O, Arai F, Iwamoto K, Okada S, et al. Bifurcation of osteoclasts and dendritic cells from common progenitors. *Blood* 98:2544-2554 (2001).

Naito, M., Hasegawa G, Takahashi K. Development, differentiation, and maturation of Kupffer cells. *Microsc Res Tech* 39:350-364 (1997).

Niyonsaba, F., Iwabuchi K, Someya A, Hirata M, Matsuda H, et al. A cathelicidin family of human antibacterial peptide LL-37 induces mast cell chemotaxis. *Immunology* 106:20-26 (2002).

Nuttall, M.E., Gimble JM. Controlling the balance between osteoblastogenesis and adipogenesis and the consequent therapeutic implications. *Curr Opin Pharmacol* 4:290-294 (2004).

Ong, P.Y., Ohtake T, Brandt C, Strickland I, Boguniewicz M, et al. Endogenous antimicrobial peptides and skin infections in atopic dermatitis. *N Engl J Med* 347:1151-1160 (2002).

Palucka, K.A., Taquet N, Sanchez-Chapuis F, Gluckman JC. Lipopolysaccharide can block the potential of monocytes to differentiate into dendritic cells. *J Leukoc Biol* 65:232-240 (1999).

Puig-Kroger, A., Sanz-Rodriguez F, Longo N, Sanchez-Mateos P, Botella L, et al. Maturation-dependent expression and function of the CD49d integrin on monocyte-derived human dendritic cells. *J Immunol* 165:4338-4345 (2000).

Randolph, G.J., Inaba K, Robbiani DF, Steinman RM, Muller WA. Differentiation of phagocytic monocytes into lymph node dendritic cells in vivo. *Immunity* 11:753-761 (1999).

Rehman, J., Li J, Orschell CM, Mar. KL. Peripheral blood "endothelial progenitor cells" are derived from monocyte/macrophages and secrete angiogenic growth factors. *Circulation* 107:1164-1169 (2003).

Romani, N., Reider D, Heuer M, Ebner S, Kampgen E, et al. Generation of mature dendritic cells from human blood. An improved method with special regard to clinical applicability. *J Immunol Methods* 196:137-151 (1996).

Sallusto, F., Lanzavecchia A. Efficient presentation of soluble antigen by cultured human dendritic cells is maintained by granulocyte/macrophage colonystimulating factor plus interleukin 4 and downregulated by tumor necrosis factor alpha. *J Exp Med* 179:1109-1118 (1994).

Schaller-Bals, S., Schulze A, Bals R. Increased levels of antimicrobial peptides in tracheal aspirates of newborn infants during infection. *Am J Respir Crit Care Med* 165:992-995 (2002).

Schmeisser, A., Garlichs CD, Zhang H, Eskafi S, Graffy C, et al. Monocytes coexpress endothelial and macrophagocytic lineage markers and form cord-like structures in Matrigel under angiogenic conditions. *Cardiovasc Res* 49:671-680 (2001).

Scott, M.G., Davidson DJ, Gold MR, Bowdish D, Hancock RE. The human antimicrobial peptide LL-37 is a multifunctional modulator of innate immune responses. *J Immunol* 169:3883-3891 (2002).

Servet-Delprat, C., Arnaud S, Jurdic P, Nataf S, Grasset MF, et al. Flt3+ macrophage precursors commit sequentially to osteoclasts, dendritic cells and microglia. *BMC Immunol* 3:15 (2002).

Shapiro, F. Bone development and its relation to fracture repair. The role of mesenchymal osteoblasts and surface osteoblasts. *Eur Cell Mater* 15:53-76 (2008).

Singhatanadgit, W., Salih, V., and Olsen, I. Up-regulation of bone morphogenetic protein receptor IB by growth factors enhances BMP-2-induced human bone cell functions. *J Cell Physiol* 209:912-922 (2006).

Sorensen, M.G., Henriksen K, Schaller S, Henriksen DB, Nielsen FC, et al. Characterization of osteoclasts derived from CD14+ monocytes isolated from peripheral blood. *J Bone Miner Metab* 25:36-45 (2007).

Sorensen, O., Arnljots K, Cowland JB, Bainton DF, Borregaard N The human antibacterial cathelicidin, hCAP-18, is synthesized in myelocytes and metamyelocytes and localized to specific granules in neutrophils. *Blood* 90:27962803 (1997).

Sorensen, O., Bratt T, Johnsen AH, Madsen MT, Borregaard N. The human antibacterial cathelicidin, hCAP-18, is bound to lipoproteins in plasma. *J Biol Chem*. pp. 22445-22451 (1999).

Sorensen, O.E., Cowland JB, Theilgaard-Monch K, Liu L, Ganz T, et al. Wound healing and expression of antimicrobial peptides/polypeptides in human keratinocytes, a consequence of common growth factors. *J Immunol* 170:5583-5589 (2003).

Sorensen, O.E., Follin P, Johnsen AH, Calafat J, Tjabringa GS, et al. Human cathelicidin, hCAP-18, is processed to the antimicrobial peptide LL-37 by extracellular cleavage with proteinase 3. *Blood* 97:3951-3959 (2001).

Teitelbaum, S.L. Bone resorption by osteoclasts. *Science* 289:1504-1508 (2000).

Teitelbaum, S.L., Ross FP. Genetic regulation of osteoclast development and function. *Nat Rev Genet* 4:638-649 (2003).

Tjabringa, G.S., Aarbiou J, Ninaber DK, Drijfhout JW, Sorensen OE, et al. The antimicrobial peptide LL-37 activates innate immunity at the airway epithelial surface by transactivation of the epidermal growth factor receptor. *J Immunol* 171:6690-6696 (2003).

Tosello, V., Zamarchi R, Merlo A, Gorza M, Piovan E, et al. Differential expression of constitutive and inducible proteasome subunits in human monocytederived DC differentiated in the presence of IFN-alpha or IL-4. *Eur J Immunol* 39:56-66 (2009).

Urbich, C., Heeschen C, Aicher A, Dernbach E, Zeiher AM, et al. Relevance of monocytic features for neovascularization capacity of circulating endothelial progenitor cells. *Circulation* 108:2511-2516 (2003).

van der Does, A.M., Beekhuizen H, Ravensbergen B, Vos T, Ottenhoff TH, et al. LL-37 directs macrophage differentiation toward macrophages with a proinflammatory signature. *J Immunol* 185:1442-1449 (2010).

Verreck, F.A., de Boer T, Langenberg DM, Hoeve MA, Kramer M, et al. Human IL-23-producing type 1 macrophages promote but IL-10-producing type 2 macrophages subvert immunity to (myco)bacteria. *Proc Natl Acad Sci U S A* 101:4560-4565 (2004).

Waskow, C., Liu K, Darrasse-Jeze G, Guermonprez P, Ginhoux F, et al. The receptor tyrosine kinase Flt3 is required for dendritic cell development in peripheral lymphoid tissues. *Nat Immunol* 9:676-683 (2008).

Yu, Y., Yang, J.L., Chapman-Sheath, P.J., and Walsh, W.R. TGF-beta, BMPS, and their signal transducing mediators, Smads, in rat fracture healing. *J Biomed Mater Res* 60:392-397 (2002).

Yuasa, K., Mori K, Ishikawa H, Sudo A, Uchida A, et al. Characterization of two types of osteoclasts from human peripheral blood monocytes. *Biochem Biophys Res Commun* 356:354-360 (2007).

Zhang, Z., Cherryholmes G, Chang F, Rose DM, Schraufstatter I, et al. Evidence that cathelicidin peptide LL-37 may act as a functional ligand for CXCR2 on human neutrophils. *Eur J Immunol* 39:3181-3194 (2009).

Zhang, Z., Cherryholmes G, Mao A, Marek C, Longmate J, et al. High plasma levels of MCP-1 and eotaxin provide evidence for an immunological basis of fibromyalgia. *Exp Biol Med (Maywood)* 233:1171-1180 (2008b).

Zhang, Z., Cherryholmes G, Shively JE. Neutrophil secondary necrosis is induced by LL-37 derived from cathelicidin. *J Leukoc Biol* 84:780-788 (2008a).

Zhao, Y., Glesne D, Huberman E. A human peripheral blood monocyte-derived subset acts as pluripotent stem cells. *Proc Natl Acad Sci USA* 100:2426-2431 (2003).

Zhou, L.J., Tedder TF. CD14+ blood monocytes can differentiate into functionally mature CD83+ dendritic cells. *Proc Natl Acad Sci USA* 93:2588-2592 (1996).

\* cited by examiner

GENERATION OF NOVEL BONE FORMING CELLS (MONOOSTEOPHILS) FROM LL-37 TREATED MONOCYTES

CROSS-REFERENCE TO RELATED APPLICATIONS

This application claims the benefit of U.S. Provisional Patent Application No. 61/388,471, filed Sep. 30, 2010, which is incorporated herein in its entirety.

STATEMENT REGARDING FEDERALLY SPONSORED RESEARCH

The invention was made with Government support under Grant No. CA84202 awarded by the National Institutes of Health (NIH). The Government has certain rights in the invention

BACKGROUND

Bone generation and maintenance involves osteoblasts, osteoclasts, and osteocytes which originate from unique precursors and rely on key growth factors for differentiation. However, there is an incomplete understanding of bone forming cells during wound healing.

Many substances such as cytokines, chemokines, and other effectors are associated with wound repair. One such substance, hCAP-18, has multiple effects on monocytes including the induction of migration (De et al. 2000; Zhang et al. 2009) and differentiation of monocytes to dendritic cells (DCs) (Davidson et al. 2004). hCAP-18 is the only human member of the cathelicidin family of antimicrobial peptides known to date (Sorensen et al 1997). LL-37, the proteolytically (proteinase 3) active product of hCAP-18, has been demonstrated to mediate a wide variety of immune and inflammatory functions, including wound repair. Release of LL-37 increases during inflammation, including that resulting from trauma and bone fracture. Growth factors involved in the process of wound healing were shown to induce LL-37 expression (Sorensen et al. 2003). In vitro, LL-37 was shown to activate endothelial cells resulting in increased proliferation and formation of vessel-like structures, while in vivo cathelicidin (CRAMP)-deficient mice showed decreased vascularization during wound repair (Kocaulla et al. 2003). LL-37 promotes re-epithelialization of healing skin (Tjabrina a et al. 2003) and anti-LL-37 antibodies inhibit re-epithelialization of skin wounds (Heilborn et al. 2003). Furthermore, LL-37 induces migration of human peripheral blood monocytes, neutrophils, CD4+ T cells, and mast cells (De et al. 2000; Zhang et al. 2009; Agerberth et al. 2000; Niyonsaba et al. 2002) and influences the expression of over 40 genes in murine RAW 264.7 macrophage cells, some of which are involved in bone formation, including the bone morphogenetic protein (BMP) 1, BMP-2, and BMP-8a (Scott et al. 2002).

Bone generation, maintenance and healing are complicated processes in which osteoblasts, osteoclasts, and osteocytes play important roles. Osteoblasts, which are derived from mesenchymal stem cells (MSCs) (Nuttall & Gimble 2004), express marker genes for bone sialoprotein (BSP) and osteocalcin (OC). Osteoclasts, which are derived from monocytes by the action of macrophage colony-stimulating factor (M-CSF) and receptor activator of nuclear factor κB ligand (RANKL), affect bone resorption by removing its mineralized matrix and breaking up the organic bone (Lacey et al. 1998). In addition to these two types of cells, the bone contains osteocytes which are trapped in the bone matrix and cease to generate osteoid and mineralized matrix. The function of osteocytes is considered as inactive osteoblasts or bone lining cells (Manolagas 2000) that undergo programmed cell death (Manolagas 2000; Jilka et al. 1998). Although much is known about the role of osteoblasts and osteoclasts in new bone formation and remodeling of existing bone, less is known about the role of these or other cells in bone repair and wound healing. (Khosla et al. 2008) Therefore, discovery and characterization of novel bone-forming cells involved in bone formation is desired to meet the unfilled clinical needs of increasing bone mass in bone injuries, malformations and diseases is desired.

SUMMARY

In one embodiment, a monocyte derived bone-forming cell population is provided. In one embodiment, the cell population comprises an isolated monocyte cell population treated with an effective dose of LL-37. In one embodiment, the cell population expresses osteocalcin (OC), osteonectin (ON), bone sialoprotein II (BSP II), osteopontin (OP), RANK, RANKL, MMP-9, tartrate resistant acid phosphatase (TRAP), and cathepsin K (CK). In one embodiment, the effective dose of LL-37 for the cell population is between about 1.25 μM and 10 μM. In another embodiment, the effective dose of LL-37 for the cell population is about 5 μM.

In another embodiment, a method of producing a population of monocyte-derived bone-forming cells is provided. The method comprises isolating a population of monocytes from a blood sample from a subject; treating the isolated monocytes with an effective dose of LL-37; and culturing the LL-37 treated monocytes until they differentiate into the population of monocyte-derived bone-forming cells. In one embodiment, the effective dose of LL-37 for the cell population is between about 1.25 μM and 10 μM. In another embodiment, the effective dose of LL-37 for the cell population is about 5 μM.

In some embodiments, the monocyte-derived bone-forming cell population is used to generate new bone in vitro or in vivo. In other embodiments, the new bone is derived from an autologous blood sample, obtained from a subject in need of bone repair or from an allogenic blood sample from a donor subject. In other embodiments, the monocyte-derived bone-forming cells are used in conjunction with a prosthetic device.

In another embodiment, a method of treatment for a bone injury or bone disease is provided. The method comprises administering a therapeutically effective amount of a composition to a subject having the bone injury or disease, the composition comprising a population of monoosteophils.

In some embodiments, the monoosteophils are a monocyte derived bone-forming cell population, comprising an isolated monocyte cell population treated with an effective dose of LL-37. In some embodiments, the effective dose of LL-37 is between about 1.25 μM and 10 μM. In other embodiments, the effective dose of LL-37 is about 5 mM.

In some embodiments, the bone injury is a fracture or a pathological fracture. In other embodiments, the bone disease is osteoporosis, osteomalacia, paget's disease, osteitis, osteogenesis imperfecta, benign bone tumors and cysts, secondary malignant bone tumors, primary malignant bone tumors, rickets, bone metabolic disorders, hypochondrogenesis, or periodontal disease.

In some embodiments the composition is administered directly to the injury or disease site by any suitable route of administration, as described further below. In other embodiments, the composition further comprises an additional therapeutic compound to induce bone formation. In some embodiments, the composition further comprises a biocompatible carrier. In other embodiments, the population of monoosteophils is derived from the subject requiring treatment or from a donor. In the case where the population of monoosteophils is derived from a donor, the composition may further comprise an immunosuppressive drug or agent.

BRIEF DESCRIPTION OF THE DRAWINGS

FIGS. 4A-4D illustrate results after 3 weeks of incubation, FIGS. 4E-4H illustrate results after 7 weeks of incubation. After incubation for 3 weeks, cells were removed with bleach and observed by phase contrast microscopy (magnification 200×, A, B) or scanning electron microscopy (SEM) (C, D). Pit formation was shown on the disc incubated with M-CSF/RANKL-differentiated monocytes (A). Refractile specks were shown on the disc incubated with LL-37-differentiated monocytes (B). SEM showed the refractile specks are built-up granules with a shallow absorbed zone (C, D). After incubation for 7 weeks, pit formation and osteoclast are shown on the disc incubated with M-CSF/RANKL differentiated monocytes by using SEM (E), and built-up structures and cells are shown on the disc of LL-37-differentiated monocytes (F-H). Monocytes at concentration of $1 \times 10^6$/mL were incubated with 5 µM LL-37 or MCSF/RANKL (both at 25 ng/mL).

DETAILED DESCRIPTION

Figure 1:
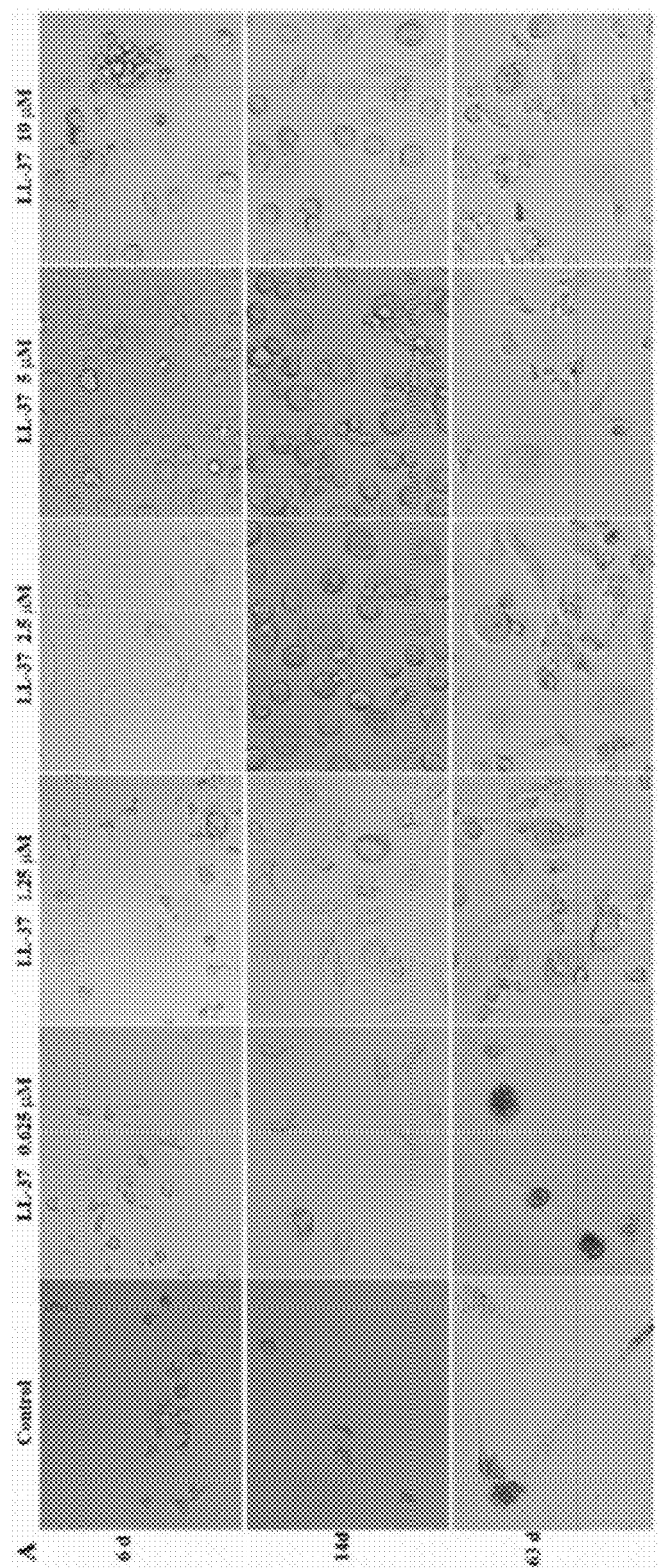
FIG. 1 shows exemplary photographs of phase contrast microscopy (magnification 200×) illustrating cell morphology of negatively isolated monocytes ($1 \times 10^6$ cells/mL) in the absence (control) or presence of increasing concentrations of LL-37 (0.625 µM, 1.25 µM, 2.5 µM, 5 µM, 10 µM) after 6 days, 14 days or 63 days of incubation.

A population of bone-forming monoosteophils and methods of generating monoosteophils are provided herein. The monoosteophils produced by the methods described are useful in providing a source of bone-forming cells for treatment of bone injuries or bone diseases or other bone malformations or pathologies.

Monocytes play an important role in the formation of new blood vessels during wound repair (Rehman et al. 2003; Urbich et al. 2003; Schmeisser et al. 2001; Fernandez et al. 2000) and often differentiate into tissue specific lineages as required by the tissue of injury (Kuwana et al. 2003). Given the plasticity of monocytes in wound repair, it was investigated as to whether, in addition to their role in bone remodeling as monocyte-derived bone absorbing osteoclasts, they may also contribute to bone repair as bone forming cells such as monoosteophils, described herein. To investigate this possibility, the response of monocytes to effectors of wound repair was examined.

As further described below, LL-37 treated monocytes form large adherent round cells after 6 days in culture, followed by the formation of large adherent round and irregular cells after 28 days in culture. Growth of LL-37-differentiated monocytes on osteologic discs for 7 weeks reveal bone-like nodule formation by scanning electron microscopy (SEM) and in vivo transplantation studies in NOD/SCID mice show that LL-37-differentiated monocytes form bone-like structures similar to endochondral bone formation. The ability to culture these cells in vitro has wide ranging applications in the clinic including augmenting repair of broken bones and treatment of osteoporosis.

In one embodiment, a population of monoosteophils may be generated by culturing a population of isolated monocytes in a composition comprising a medium capable of supporting the growth of said monocytes, such as RPMI 1640 medium supplemented with fetal bovine serum (FBS), and an effective amount of LL-37 to induce differentiation of the isolated monocytes. The monoosteophils may be combined with other cells such as mesenchymal stem cells to enhance their properties.

Monocytes that may be used to generate a population of monoosteophils may be isolated from a bone marrow sample or a blood or other bodily fluid sample of a subject. Isolation may be accomplished by any suitable method for separating and concentrating the monocytes from other cells, such as the use of cell-specific antibodies that recognize and bind antigens present on, monocytes and other stem cell or blood cells found in blood or bone marrow. These include both positive selection (selecting the target cells), negative selection (selective removal of unwanted cells), or combinations thereof. Intracellular markers such as enzymes may also be used in selection using molecules which fluoresce when acted upon by specific enzymes. The subject may be a human, horse, dog, cat, mouse, rat, rabbit, or any other animal susceptible to bone malformation, fracture or disease that may benefit from the methods described herein.

As used herein, an "effective amount" of a substance is an amount of the substance that produces a desired effect in a cell culture system. The results of the studies described in the examples below showed that LL-37 at the concentrations of approximately ≧1.25 µM and approximately ≦10 µM can induce monocyte differentiation. These levels of LL-37 occur naturally during inflammation. Therefore, according to embodiments described herein, the desired effect is induction of differentiation caused by LL-37 that stimulates monocytes to transform into bone-forming monoosteophils, and the effective amount is between about 1.25 µM and 10 µM. In some embodiments, the effective amount is about 1.25 µM, about 2.5 µM, about 5 µM or about 10 µM. In other embodiments, the effective amount is between about 1.25 µM and 5 µM, about 2.5 µM and 5 µM, about 2.5 µM and 7.5 µM, or about 5 µM and 10 µM. In one embodiment, the effective amount is about 5 µM.

According to the embodiments of the disclosure, monoosteophils are a distinct cell type that differs from other bone forming cells and from other monocyte-derived cells. Monoosteophils, or LL-37-differentiated monocytes, are distinct from monocyte-derived macrophages, dendritic cells (DCs), and osteoclasts according to their morphology, surface markers, and/or cytokine profiles. In addition, they do not express surface markers of the MSC lineage, clearly distinguishing them from the conventional precursors of osteoblasts, but do express BMP-4 and BMP-7, which are important in the differentiation of MSCs into osteoblasts. LL-37-differentiated monocytes express proteins of both the osteoblast and osteoclast lineage including osteocalcin (OC), osteonectin (ON), bone sialoprotein II (BSP II), osteopontin (OP), RANK, RANKL, MMP-9, tartrate resistant acid phosphatase (TRAP), and cathepsin K (CK).

Bone is a dynamic tissue that undergoes constant remodeling in which old bone is degraded by osteoclasts, the bone-resorbing cell, and subsequently replaced by new bone formed by osteoblasts, the bone-forming cell (Teitelbaum 2000; Teitelbaum & Ross 2003; Ducy et al. 2000). Osteoblasts are derived from mesenchymal stem cells (MSCs) through a multi-step differentiation pathway (Ducy et al. 2000). In the examples described below, the data suggests that LL-37-differentiated monocytes (monoosteophils), which have different cell surface markers compared to MSCs, are a type of bone forming cell that is distinct from other bone-forming cells. Moreover, monoosteophils express some characteristic proteins of both osteoblasts and osteoclasts, including OC, ON, BSP II, OP, TRAP, CK, MMP-9, RANK, and RANKL. Furthermore, LL-37-differentiated monocytes (monoosteophils) express BMP-4 and BMP-7, which are important in the differentiation of MSCs into osteoblasts.

Both monoosteophils and osteoclasts are differentiated from monocytes. When monocytes are treated with M-CSF/RANKL, they differentiate into osteoclasts that exhibit a bone resorbing phenotype, but when monocytes are treated with LL-37, they produce monoosteophils with a bone forming phenotype. Thus, the environmental niche of monocytes may determine their ultimate phenotype. In the bone marrow where monocytes are exposed to M-CSF and RANKL, they become osteoclasts, but in an external wound-healing environment exposed to LL-37, they become monoosteophils. Circulating monocytes play an important role in development and homeostasis, in part via the removal of apoptotic cells and scavenging of toxic compounds (Franc et al. 1996). Circulating monocytes also are accessory cells, linking inflammation and the innate defense against microorganisms to adaptive immune responses. In fact, circulating monocytes are a considerable systemic reservoir of myeloid precursors for the renewal of some tissue macrophages, antigen-presenting DCs (Randolph et al. 1999; Waskow et al. 2008; Geissmann et al. 2003).

It has been reported that circulating monocytes have the potential to differentiate to a variety of cell types such as multipotential cells and endothelial cells other than phagocytes (Kuwana et al. 2003; Zhao et al. 2003). For example, monocyte-derived multipotential cells (MOMC), having a unique phenotype positive for CD14, CD45, CD34, and type I collagen with a fibroblast-like morphology, can be obtained in cultures of peripheral blood mononuclear cells (PBMC) for 7 to 10 days on fibronectin-coated plastic plates supplemented with 10% fetal bovine serum as the only source of growth factors (Kuwana et al. 2003). Moreover, MOMC are spindle shape cells and monoosteophils contain both large round and irregular shaped cells. Furthermore, MOMC are CD14, CD45, CD34 positive, while monoosteophils are CD45 positive but CD14 and CD34 negative. Thus, monoosteophils are distinct from MOMC regarding generation, morphology, and surface markers.

LL-37 is a potent modifier of DC differentiation and maturation (Davidson et al. 2004; Kandler et al. 2006; Bandholtz et al. 2006). For example, monocytes that were co-cultured for 7 days with LL-37 and IL-4/GM-CSF were differentiated into DCs (Davidson et al. 2004); treatment of GM-CSF/IL-4-derived immature DCs with LL-37 and LPS suppressed the maturation and activation of DCs by TLR ligands (Kandler et al. 2006); GM 18 CSF/IL-4-derived immature DCs treated with LL-37 undergo internalization and subsequent localization of LL-37 in the cytoplasmic and nuclear compartments, causing an increased expression of HLA-DR and CD86 (Bandholtz et al. 2006). As shown in the studies described below, monoosteophils do not share dendritic cell markers and morphology with either GM-CSF/IL-4- or GMCSF/IFNα-derived DCs. In another study (von Does et al., 2010), monocytes that were treated with either GM-CSF or M-CSF plus LL-37 differentiated to macrophages with an inflammatory phenotype. More importantly, the main difference between these studies and other studies is that LL-37 was used as the sole factor for monocyte differentiation instead of combining LL-37 with IL-4/GM-CSF, treatments which may have directed differentiation along another lineage. It is noted that monoosteophils may be generated for any use or method described herein may by an effective amount any suitable substance having an action that is equivalent to LL-37. Such substances may include other synthetic or natural proteins or peptides, small molecules, constructs, or functional portions or fragments of LL-37.

Plasma has been reported to contain hCAP-18 bound to lipoproteins at a concentration of 1.2 µg/mL (Sorensen et al. 1999), suggesting that the precursor to LL-37 is constantly released into the bloodstream but in an inactive form (Sorensen et al. 2001). LL-37 can be detected at concentrations of approximately 5 µg/mL in BALF of healthy infants and is up-regulated to 20 µg/mL from infants with lung infections (Schaller-Bals et al. 2002). Likewise, the hCAP-18 concentration in seminal plasma is in the range of 41.8-142.8 µg/mL (Malm et al. 2000), and LL-37 is present in psoriatic skin plaques at a median concentration of 304 µM (Ong et al. 2002). To date, there are no known reports regarding LL-37 concentration in the bone marrow or in bone undergoing repair. Due to the situation of increased LL-37 release in the inflammation (Frohm et al. 1996), the data below suggests that the action of LL-37 on circulating monocytes may play an important role in bone fracture and repair, since monoosteophils have the ability to use existing bone material to build new bone and function both in vivo and in vitro. These cells may have an important physiological and pathophysiological function. In addition, the ability of these cells to produce new bone in vitro has important implications for clinical situations demanding the rapid production of new bone in the case of unrepaired breaks or osteoporotic lesions or other bone injuries, malformation or disease as described further below.

According to some embodiments of the disclosure, monoosteophils may be used to generate new bone in vivo or in vitro, and may be used to repair or reconstruct of one or more bones in a subject. Currently, osteoblasts are utilized for bone formation, but such cells are generated from mesechymal stem cells which are isolated from bone marrow in small numbers. The cells and methods described herein simplify the process of obtaining bone-forming cells in large numbers suitable for research and clinical purposes.

In one embodiment, the monoosteophils may be used to generate a bone graft composition that is used to enhance, augment or replace bone material in a cosmetic or reconstructive procedure or surgery. Thus, a method for enhancement, augmentation or replacement of bone is provided. In one embodiment, such a method may include surgical implantation of a bone graft composition derived from a population of monoosteophils to enhance, augment or replace existing or previously existing bone material. In some aspects a cosmetic procedure may include one or more voluntary procedures that include, but are not limited to enhancement, shaping, sculpting or augmentation of one or more bones such as maxillofacial bones (e.g., cheek implants, jaw implants, chin implants), shoulder bones or other misshapen, non-symmetric or underdeveloped/weak bones that a subject desires to change for aesthetic or other cosmetic reasons. In some aspects, a patient may desire to augment one or more bones to create symmetrical facial or other skeletal features. In other aspects, a reconstructive procedure may be a desired or necessary procedure to correct defects due to genetic deformities or trauma resulting in bone tissue that is fractured beyond use or entirely lost. The bone graft composition may include new bone tissue that is generated in vitro and may be grown in culture alone or on a support matrix. Further, the bone graft composition may be grown in a desired shape using plates or support matrices in such a shape.

In other embodiments, monoosteophils may be used in methods for treating a bone injury or bone disease. A method for treating a bone injury, disease or malformation according to the embodiments described herein may include administering a therapeutically effective amount of a therapeutic composition to a subject having the bone injury, disease or malformation. In some embodiments, the therapeutic composition may include a population of monoosteophils produced by the methods described herein. In other embodiments, the therapeutic composition may include LL-37 to induce resident or recruited monocytes to form a population of monoosteophils at a wound site in vivo. In some embodiments, the therapeutic composition may be mixed with a population of bone marrow stem cells to create a hematopoetic environment that would promote expansion of the bone marrow stem cells.

In some embodiments, the monoosteophils and methods of their use as described herein may be used to deliver a gene product (e.g., RNA, protein, polypeptide, peptide, antibody or functional fragment thereof, antigen) to the site of administration. To accomplish this, a nucleotide sequence may be delivered to one or more monoosteophils by a vector (e.g., viral vector, plasmid). The resulting gene product produced by the monoosteophils may be a therapeutic substance or other substance that works in conjunction with the monoosteophils to enhance the repair or augmentation of the existing, damaged or diseased tissue, to provide support for the cell proliferation necessary for reparation, enhancement or augmentation of the tissue at the predetermine site, and to enhance adherence of the monoosteophils to the site of repair, enhancement or augmentation.

As used herein, a "therapeutically effective amount" is an amount of a therapeutic compound that produces a desired therapeutic effect in a subject, such as preventing or treating a target condition, alleviating symptoms associated with the condition, or producing a desired physiological effect. The precise therapeutically effective amount is an amount of the composition that will yield the most effective results in terms of efficacy of treatment in a given subject. This amount will vary depending upon a variety of factors, including but not limited to the characteristics of the therapeutic compound (including activity, pharmacokinetics, pharmacodynamics, and bioavailability), the physiological condition of the subject (including age, sex, disease type and stage, general physical condition, responsiveness to a given dosage, and type of medication), the nature of the pharmaceutically acceptable carrier or carriers in the formulation, and the route of administration. One skilled in the clinical and pharmacological arts will be able to determine a therapeutically effective amount through routine experimentation, namely by monitoring a subject's response to administration of a compound and adjusting the dosage accordingly. For additional guidance, see Remington: The Science and Practice of Pharmacy 21$^{st}$ Edition, Univ. of Sciences in Philadelphia (USIP), Lippincott Williams & Wilkins, Philadelphia, Pa., 2005.

The therapeutic composition or bone graft composition may include a biocompatible carrier or matrix material to promote adherence of the monoosteophils or new bone tissue to the existing tissue, to further enhance the repair or augmentation of the existing, damaged or diseased tissue, to provide support for the cell proliferation necessary for reparation, enhancement or augmentation of the tissue at the predetermine site, and to enhance adherence of the monoosteophils to the site of repair, enhancement or augmentation. Suitable carrier materials may include, but are not limited to, proteins such as collagen, gelatin, fibrin/fibrin clots, demineralized bone matrix (DBM), Matrigel® and Collastat®; carbohydrates such as starch, polysaccharides, saccharides, amylopectin, Hetastarch, alginate, methylcellulose and carboxymethyl-cellulose; proteoglycans, such as hyaluronate; agar; synthetic polymers, including polyesters (especially of normal metabolites such as glycolytic acid, lactic acid, caprolactone, maleic acid, and glycols), polyethylene glycol, polyhydroxyethylmethacrylate, polymethylmethacrylate, poly (amino acids), polydioxanone, and polyanhydrides; ceramics, such as tricalcium phosphate (TCP), hydroxyapatite (HA), alumina, zirconia, bone mineral and gypsum; glasses such as Bioglass, A-W glass, and calcium phosphate glasses; metals including titanium, Ti-6Al-4V, cobalt-chromium alloys, stainless steel and tantalum; and hydrogel matrices. In accordance with some embodiments, the carrier is selected from a material that is biodegradable or bioresorbable.

In other embodiments, the therapeutic composition or bone graft composition may include an additional therapeutic compound to induce bone formation (or osteogenesis). In some embodiments, the monoosteophils or new bone tissue may be administered in conjunction with anti-resorptive medications such as bisphosphonates (e.g., sodium alendronate, ibandronate and risedronate), hormones (e.g., calcitonin and estrogens) and selective estrogen receptor modulators (e.g., raloxifene). In other embodiments, the monoosteophils or new bone tissue may be administered or implanted in conjunction with bone anabolic agents such as teriparatide, calcium salts (e.g., calcium citrate, lactate, gluconate and calcium carbonate), and sodium fluoride. In other embodiments, the monoosteophils may be administered in conjunction with RANKL inhibitors (e.g., denosumab), strontium ranelate, or nutrient supplements (e.g., calcium, vitamin D). In one embodiment, the additional therapeutic compound may include LL-37 to induce differentiation of resident or recruited monocytes present at a wound site. Alternatively, LL-37 may be administered to a wound site alone. In another embodiment, the therapeutic composition or bone graft composition may include a population of bone marrow stem cells to create a hematopoetic environment that would allow expansion of the bone marrow stem cells.

In some embodiments, the new bone may be autologous, meaning that the monoosteophils used to generate the new bone are derived from monocytes obtained and isolated from the subject requiring the treatment, thereby avoiding immune rejection of the monoosteophils. In other embodiments, the new bone may be allogenic, meaning that the monoosteophils used to generate the new bone are derived from a donor subject. Allogenic monoosteophils or new bone derived therefrom may be harvested from donors and stored in a tissue bank and used if needed in an emergency situation or in other situations where autologous monoosteophils or new bone cannot be obtained. When allogenic monoosteophils or new bone are used in the methods, treatments and procedures described herein, the therapeutic composition or bone graft composition should also include an immunosuppressive drug or agent to reduce or prevent rejection of the donor monoosteophils. The immunosuppressive drug or agent may be any suitable pharmaceutical agents that inhibits or interferes with normal immune function. Examples of immunosuppressive agents suitable with the methods disclosed herein include, but are not limited to cyclosporine A, myophenylate mofetil, rapamicin, and anti-thymocyte globulin.

In some embodiments, the composition may be administered systemically or may be administered directly to the site of injury or disease. The delivery may be by any suitable route of administration, including, but not limited to intradermal, subcutaneous, intravenous, intraarterial, intramuscular, intraosseous, intrathecal, intraperitoneal, or arthroscopic injection or by direct application or implantation to the site during surgery. In other embodiments, the monoosteophils may be cultured to grow bone graft material in vitro, then said bone graft may be implanted to the site of repair.

The treatment may be used for a wide range of bone injuries, malformations and diseases. In some embodiments, the injury may be due to bone fractures or other bone-related musculoskeletal injuries such as ligament, tendon or cartilage injuries, resulting from a high force impact or high stress to a bone. Such injuries may result from a high force impact or stress to a bone.

In other embodiments, the injury may be due to a pathologic fracture caused by disease. Pathologic fractures may be caused by bone disease, such as osteoporosis, osteomalacia, paget's disease, osteitis, osteogenesis imperfecta, benign bone tumors and cysts, secondary malignant bone tumors and primary malignant bone tumors. Therefore, in some embodiments, the treatments described herein may be used to treat said bone diseases to help prevent pathologic fractures.

Further, many treatments, therapies or medications can result harmful effects to bone such as bone density loss or brittleness. Examples of such treatments, therapies or medications include, but are not limited to, aluminum-containing antacids, antiseizure medications (only some) such as Dilantin® or phenobarbital, aromatase inhibitors (e.g., Arimidex®, Aromasin® and Femara®), cancer chemotherapeutic drugs, cancer radiation treatments, cyclosporine A and FK506 (Tacrolimus), glucocorticoids (e.g., cortisone and prednisone), gonadotropin releasing hormone (GnRH) (e.g., Lupron® and Zoladex®), heparin, lithium, medroxyprogesterone acetate for contraception (Depo-Provera®), methotrexate, proton pump inhibitors (PPIs) (e.g., Nexium®, Prilosec® and Prevacid®), selective serotonin reuptake inhibitors (SSRIs) (e.g., Lexapro®, Prozac® and Zoloft®), Tamoxifen® (premenopausal use), thiazolidenediones (e.g., Actos® and Avandia®), and thyroid hormones in excess. Thus, in some embodiments, the treatments described herein may be given in combination with or subsequent to these bone-harming treatments, therapies or medications discussed above. For example, treatment with monoosteophils and/or LL-37 as described herein may be used as a post-cancer therapy subsequent to treatment with chemotherapeutic drugs or radiation.

Other bone diseases and malformations that may benefit from treatment with monoosteophils may include rickets, bone metabolic disorders, hypochondrogenesis, and other bone deformation disorders resulting in bone malformations, or missing and/or underdeveloped bones. In a further embodiment, the treatments described herein may be used in dentistry to regenerate bone in the treatment of periodontal disease.

In some embodiments, a method for the use of monoosteophils in conjunction with a prosthetic device or bone graft is provided. In one embodiment, a population of monoosteophils may be used in conjunction with the bone graft compositions generated as described above. A variety of clinically useful prosthetic devices have been developed for use in bone and cartilage grafting procedures. In some embodiments, prosthetic devices that are suitable for use with monoosteophils include, but are not limited to, knee and hip replacement devices, biocompatible materials used for facial and other structural implants and dental implants, which have been and continue to be widely used in the clinic. Many of these devices are fabricated using a variety of inorganic materials having low immunogenic activity, which safely function in the body. These materials provide structural support and can form a scaffolding into which host vascularization and cell migration can occur. Attachment may be improved by seeding such prosthetic devices with bone-forming cells such as monoosteophils. This type of seeding should enhance the effectiveness of the implant and speed with which attachment occurs by providing a fertile environment into which host vascularization and cell migration can occur. For example, in surgery, they may be used to seed an area where metal pins may be placed to speed recovery or enhance implantability of bone prosthetics.

Having described the invention with reference to the embodiments and illustrative examples, those in the art may appreciate modifications to the invention as described and illustrated that do not depart from the spirit and scope of the invention as disclosed in the specification. The Examples are set forth to aid in understanding the invention but are not intended to, and should not be construed to limit its scope in any way. The examples do not include detailed descriptions of conventional methods. Such methods are well known to those of ordinary skill in the art and are described in numerous publications. Further, all references cited above and in the examples below are hereby incorporated by reference in their entirety, as if fully set forth herein.

Example 1

Generation of LL-37-Differentiated Bone-Forming Cells (Monoosteophils)

Materials and Methods

Live cell imaging. Monocytes ($1 \times 10^6$/mL) were incubated with 5 µM LL-37 for 6 days or 63 days or MCSF/RANKL for 6 days and imaged every 1 hour for 6-day LL-37- and MCSF/RANKL-differentiated cells or every 15 minutes for 63-day LL-37-differentiated cells using an Olympus IX81 inverted fluorescent microscope equipped with a Weatherstation precision control stage incubator and an Orca-ER Hammamatsu camera. Phase contrast time lapse images were obtained. Movies were processed in Slidebook 5 (data not shown). Representative frames are shown in the figures.

Reagents. Phalloidin and saponin were purchased from Sigma-Aldrich (St. Louis, Mo., USA); anti-BMP-2 (Clone 100230), anti-BMP-4 (Clone 66119), and anti-BMP-7 (Clone 164311) were purchased from R&D System (Minneapolis, Minn. 55413, USA); anti-BMP-8 (clone H-105) was purchased from Santa Cruz Biotechnology Inc (Santa Cruz, Calif. 95060); anti-CD14-FITC (clone M5E2) and isotype controls were purchased from BD Biosciences (Chicago, Ill., USA); Alexa Fluor 488 goat anti-mouse IgG (H+L), Alexa Fluor 488 goat anti-rabbit IgG (H+L), and Alexa Fluor 488 chicken anti-goat IgG (H+L) were from Invitrogen Corp (Chicago, Ill. 60690); Hard Set mounting medium with DAPI was from Vector Laboratories (Burlingame, Calif., USA); EasySep® Human Monocyte Enrichment Kit was from StemCell Technologies Inc (Vancouver, Canada); FBS and human serum were from Irvine Scientific (Santa Ana, Calif., USA); LL-37 was synthesized, prepared and stored as previous reports (Zhang et al. 2003; Zhang et al. 2008a).

Monocyte preparation and differentiation. This study was approved by the Institutional Human Subject's Review Board (City of Hope National Medical Center). Peripheral blood mononuclear cells (PBMCs) were isolated from citrated blood by centrifugation over Ficoll-Paque Plus (GE healthcare biosciences, Pittsburgh, Pa., USA) density gradient. Monocytes were separated using EasySep® Human Monocyte Enrichment Kit (StemCell Technologies Inc, Vancouver, Canada) from PBMCs. The purified monocytes were stained with anti-CD14-FITC and checked by using flow cytometry FACSCanton II. Monocytes with >95% purity were suspended at $1 \times 10^6$ cells/mL in RPMI 1640 medium supplement with 10% FBS (FBS contained <5 pg/100 mL LPS).

Cell lines. Clonogenic human MSCs were generously provided by Dr. Carlotta A. Glackin (Department of Neurosciences, City of Hope) and incubated in α-MEM supplemented with 20% fetal calf serum (FCS), 2 mM L-glutamine, and 100 µM L-ascorbate-2-phosphate as previously described (Isenmann et al. 2009).

Flow cytometry. For cell surface staining, cells were washed with PBS, blocked with 10% human serum in PBS, stained with isotype controls and antibodies described in the figures, washed 3 times with 1% BSA PBS, and analyzed with a FACSCanton II. For intracellular staining, cells were washed with PBS, fixed with 1% paraformaldehyde in PBS, permeabilized in PBS buffer containing 0.1% saponin (Sigma-Aldrich) and 2% BSA, and stained with primary isotype controls and antibodies shown in the figures. After washing with PBS containing 1% BSA and 0.1% saponin, cells were stained with secondary Alexa 488 conjugated antibodies. Stained cells were assessed with a FACSCanton II cytometer, and analyzed using Flowjo software.

Statistical analysis. Assay results are expressed as means±SE and unpaired Student's t-tests were used for comparisons. All p-values are two-sided. Data were analyzed with SPSS software (release 10.0, SPSS, Chicago, Ill., USA) and GraphPad Prism software (version 5.0, GraphPad Software, San Diego, Calif., USA).

LL-37 Induces Monocyte Differentiation and Survival.

Figure 2:
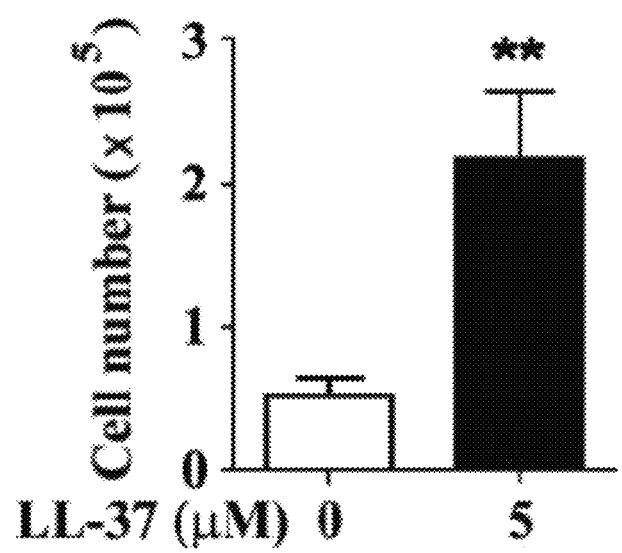
FIG. 2 is a bar graph illustrating monocyte cell number after 6 days with or without treatment with 5 µM of LL-37. Cells were harvested and counted by hemocytometer. Data (mean±SE) was from four independent experiments performed (**$p<0.01$ vs control).
Figure 3A:
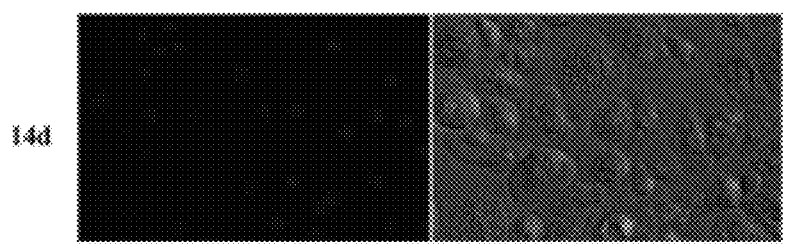
FIGS. 3A and 3B are exemplary photographs of monocytes treated with 5 µM LL-37 for 14 days (A) or 63 days (B) that were fixed, permeablized, stained with DAPI, and observed by fluorescent microscopy. Multinucleated giant cell formation was found in 63-day LL-37-treated monocytes. Images represent one of four independent experiments.
Figure 3B:
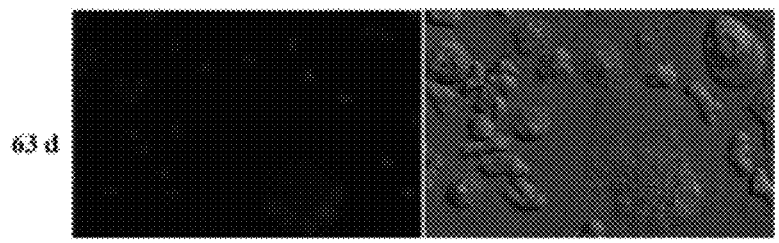

Negatively isolated monocytes at the concentration of $1 \times 10^6$/mL were incubated in RPMI 1460 medium with 10% FBS in the presence or absence of LL-37. After treatment with LL-37 for 6 days, monocytes had differentiated into large round adherent cells in comparison with untreated cells that remained as either small round suspended cells or underwent cell death (FIG. 1). The numbers of 5 µM LL-37-treated cells are significantly higher than untreated controls in agreement with loss of cells in untreated controls by cell death (FIG. 2). The maximum effect occurred at the dose of 5 µM LL-37 after which higher doses ($\geq 10$ µM) led to decreased cell numbers due to toxicity of LL-37>10 µM (Zhang et al. 2008a; Johansson et al. 1998). After 14 days, the cell number of untreated controls decreased further, but the LL-37-differentiated monocytes survived with an apparent further increase in the diameter of the round adherent cells. DAPI staining showed that LL-37-differentiated round adherent cells have a single nucleus in spite of their larger cell size (FIG. 3A). However, after continuous culture for 63 days some of the large round LL-37-differentiated monocytes became giant cells with a multinucleated characteristic similar to osteoclasts (FIG. 3B). In addition to the large round cells, the appearance of irregular shaped cells was noted at 63 days for cells treated with 1.25-10.0 µM LL-37 (FIG. 3B). To determine the relationship among the different types of cells, time lapse photography was performed and showed that the giant cells were derived from the large round cells (data not shown). There was no evidence of cell-cell fusion in the creation of giant cells. Together these analyses indicate that LL-37 can progressively differentiate monocytes into large round adherent cells at early times with giant cells and irregular shaped cells appearing at later times.

BMP-4 and BMP-7 May Play a Role in LL-37 Induced Monocyte Differentiation.

Figure 22:
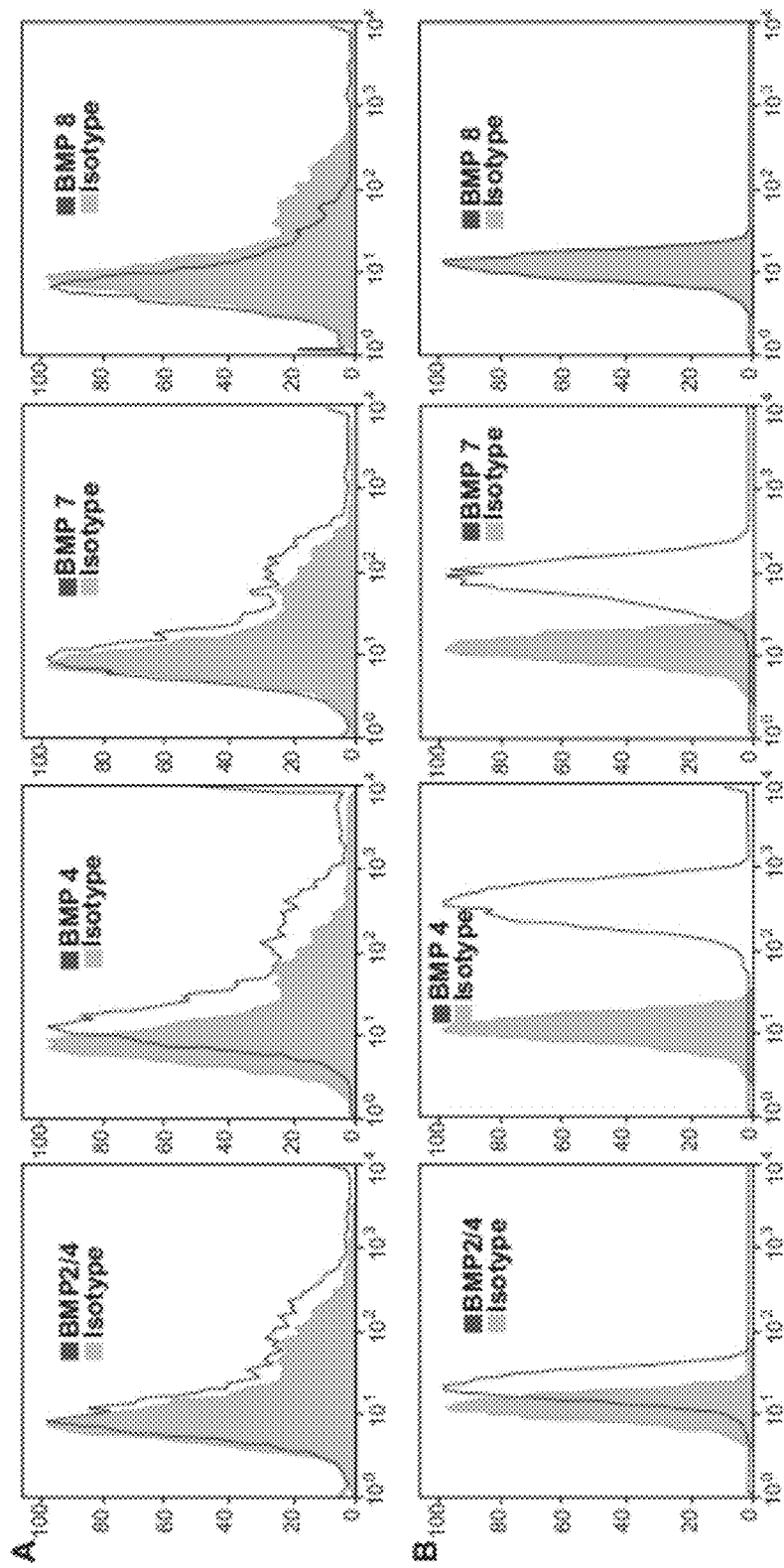
FIG. 22 shows monocytes that were incubated in the presence of LL-37 for 6 days, harvested, stained with antibodies and analyzed by flow cytometry to show surface staining (A) or were fixed, permeabilized, stained with the same antibodies as FIG. 21, and analyzed by flow cytometry to show intracellular staining. Data shown were from one of four independent experiments. Isotype control is shaded.

Bone morphogenetic proteins (BMPs), members of the transforming growth factor (TGF)-β superfamily, especially BMP-2, -4, and -7, play an essential role in skeletal development and repair (Yu et al. 2002) by promoting differentiation of MSCs into chondrocytes and osteoblasts (Singhatanadgit et al. 2006). In order to investigate the relationship of monoosteophils and BMPs, surface and intracellular staining of BMP-2, -4, -7, and -8 were analyzed by flow cytometry. Surface staining results showed that only BMP-4 is expressed in low intensity on the cell membrane of 6-day differentiated monoosteophils (FIG. 22A). However, intracellular staining showed high expression levels of BMP-4 and BMP-7, low levels of BMP-2, and no expression of BMP-8 in the cytosol (FIG. 22B). These results suggest that BMP-4 and BMP-7 may play a role in the LL-37 differentiation of monocyte into bone forming monoosteophils.

Example 2

Monoosteophils Induce In Vitro and In Vivo Bone Formation

Materials and Methods

The following the materials and methods were used in addition to those described in Example 1 above:

Reagents. Recombinant human GM-CSF, M-CSF, IL-4, IFNα, and RANKL were purchased from ProSpec Tany TechnoGene Ltd (Rehovot 76124, Israel); LPS from *E. coli* (055:B5) was obtained from Sigma-Aldrich (St. Louis, Mo.); anti-bone sialoprotein II (BSPII, Clone ID1.2), anti-osteopontin (OP, clone AKm2A1), rabbit anti-human tartrate resistant acid phosphatase (TRAP) and anti-human cathepsin K (CK) polyclonal antibodies were from Santa Cruz Biotechnology Inc (Santa Cruz, Calif. 95060); anti-CD1b FITC (Clone MT101), anti-CD16-PerCP-Cy5.5 (Clone 3G8), anti-CD14-FITC (clone M5E2), isotype controls, and BioCoat™ Osteologic™ Discs were from BD Biosciences (Chicago, Ill., USA); anti-CD1c FITC (Clone AD5-8E7) was from Miltenyi Biotec Inc (Auburn, Calif. 95602); anti-CD45 PE (clone HI30) was from eBiosciences (Dallas, Tex. 75312).

Bone resorption assay. The resorbing activity was evaluated by using BioCoat™ Osteologic™ Discs purchased from BD Biosciences as a mineral matter in 24-well plate. Monocytes were incubated with M-CSF/RANKL (both at 25 ng/mL) or 5 µM LL-37 on BioCoat™ Osteologic™ Discs for 21 days in 5% CO2 atmosphere, then cells were removed by exposure to NaOCl. The plates were washed by rinsing distilled water and pit formation was observed by light microscopy (Yuasa et al. 2007) and scanning electron microscopy (SEM). LL-37-differentiated monocytes and M-CSF/RANKL-differentiated osteoclasts were also incubated on BioCoat™ Osteologic™ Discs for 7 weeks and fixed with 2.5% glutaraldehyde in 0.1 M phosphate buffer for SEM.

Scanning electron microscopy (SEM). BioCoat™ Osteologic™ Discs fixed in 2.5% glutaraldehyde in 0.1 M phosphate buffer, pH 7.2 (buffer A) for 1 hour from bone resorption assay were washed three times in buffer A, postfixed with 1% osmium tetroxide in buffer A, then dehydrated in graded ethanol. The 100% ethanol solution was then replaced by propylene oxide, and the cells were embedded in Eponate.

Thin sections were stained with uranyl acetate and lead citrate and examined with a FEI TECNAI G2 electron microscope.

von Kossa staining of osteologic disks co-cultured with LL-37 differentiated monocytes. After 5 weeks of co-culture with control- or LL-37-differentiated monocytes, BioCoat™ Osteologic™ Discs were stained to demonstrated mineralization by using von Kossa staining according to BD Biosciences technical bulletin #444. Discs were photographed using phase contrast microscopy (magnification 200×).

In vivo transplantation studies and histological examination. These procedures were performed in accordance with specifications of an approved animal protocol (City of Hope institutional animal care and use committee). Approximately $5.0 \times 10^6$ monocytes plus LL-37 (5 µM) were mixed with 40 mg of hydroxyapatite/tricalcium phosphate (HA/TCP) ceramic powder (Zimmer Inc, Warsaw, Ind.) and then transplanted subcutaneously into the dorsal surface of 10-week-old immunocompromised NOD/SCID mice for 7 weeks (Isenmann et al 2009). $5.0 \times 10^6$ monocytes alone, LL-37 (5 µM) alone or blank control were mixed with 40 mg of hydroxyapatite/tricalcium phosphate (HA/TCP) ceramic powder as controls. Harvested implants were fixed in 10% formalin neutral buffered solution, decalcified in 10% EDTA, and embedded in paraffin. Four-micrometer-thick sections were stained with hematoxylin and eosin, and trichrome. For immunohistochemistry, sections were stained using primary mouse anti-human BSP II monoclonal (Santa Cruz Biotechnology Inc) and secondary biotinylated rabbit anti-mouse IgG.

Monoosteophils have Bone-Forming Ability In Vitro.

Figure 4:
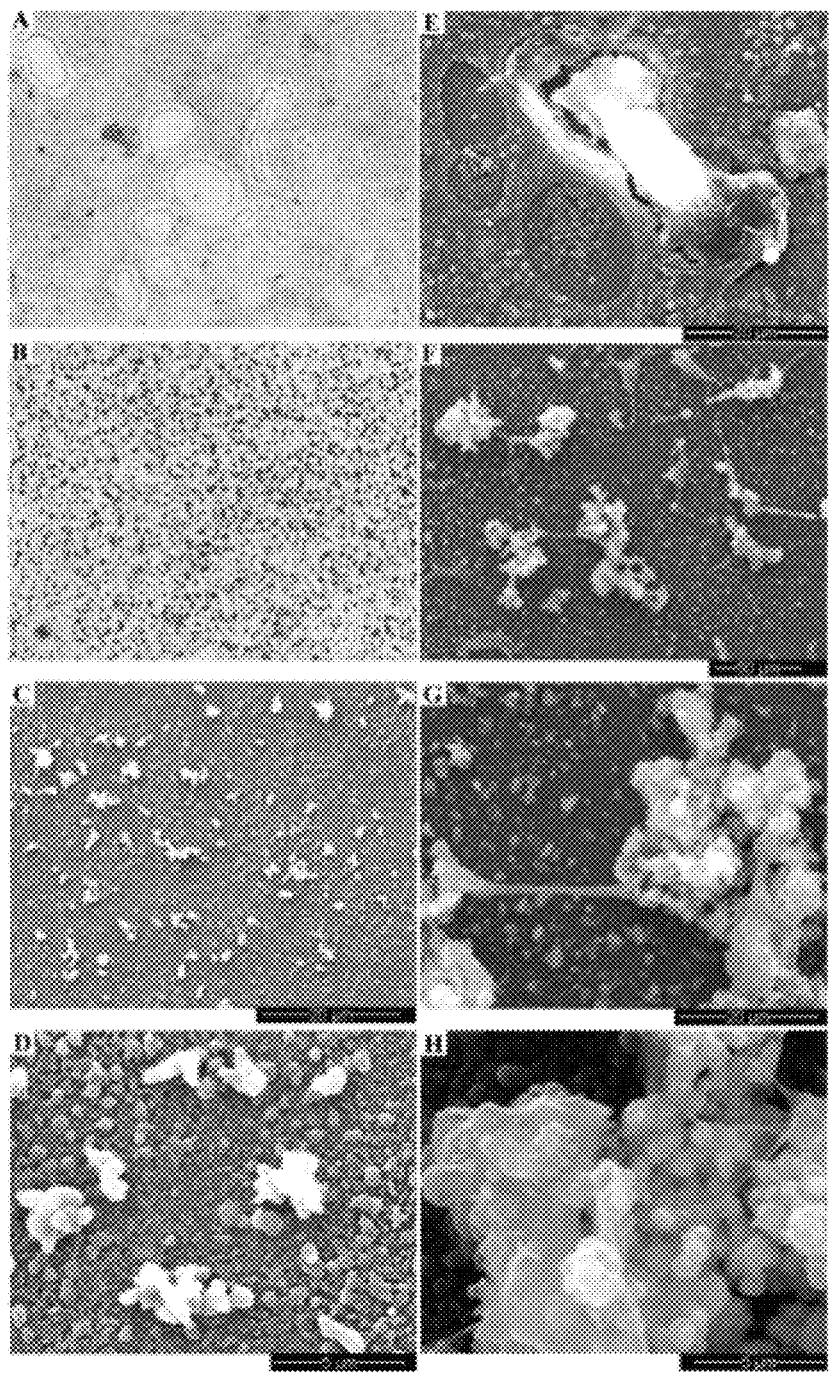
FIG. 4 shows exemplary phase contrast microscopy (A, B, 200×) and scanning electron microscopy (SEM) (C-H) images of monocytes seeded at a concentration of $1 \times 10^6$/mL incubated in the presence of M-CSF/RANKL (both at 25 ng/mL, A, E) or 5 µM LL-37 (B, C, D, F, G, H) on BioCoat™ Osteologic™ Discs in 5% CO2 atmosphere.
Figure 5:
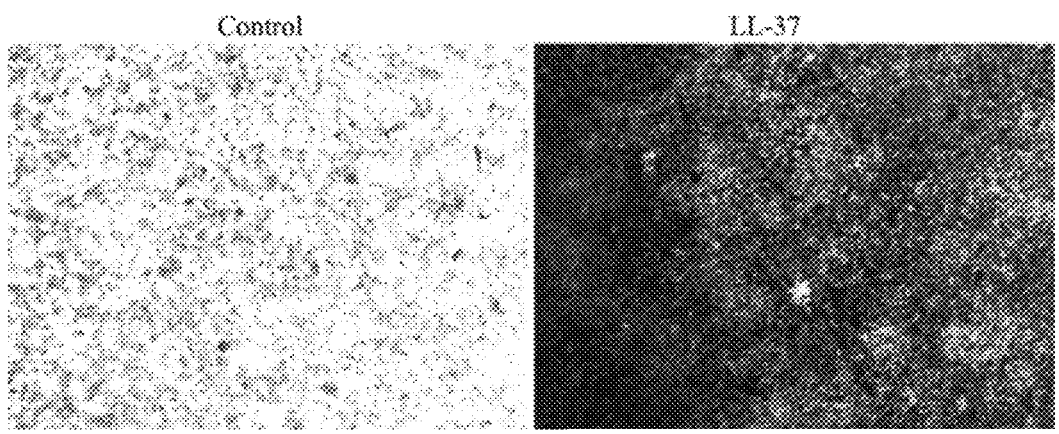
FIG. 5 shows von Kossa staining of the osteologic disks co-cultured with LL-37 differentiated monocytes demonstrating mineralization compared to untreated controls.

Culture of unfractionated peripheral-blood monocytes with M-CSF and RANKL is sufficient to induce their differentiation in vitro to osteoclasts (Teitelbaum 2000). The multinucleation characteristic of the osteoclast is the most striking morphological feature distinguishing the osteoclast from its monocyte precursor. Since LL-37-differentiated monocytes at late times have the morphology of giant cells of osteoclasts, it was likely that they would share their function, namely the dissolution/absorption of bone. BioCoat™ Osteologic™ Discs were used to evaluate the bone absorption ability of LL-37-differentiated monocytes compared to in vitro derived osteoclasts. After incubation on BioCoat™ Osteologic™ Discs for 3 weeks following removal of cells by bleach, M-CSF/RANKL-differentiated osteoclasts formed absorption pits on the BioCoat™ Osteologic™ Discs (FIG. 4A) comparable to published results (Yuasa et al. 2007). Unexpectedly, LL-37-differentiated monocytes formed refractile specks on the discs instead of classical absorption pits when viewed by phase contrast microscope (FIG. 4B). Scanning electron microscopy (SEM) analysis revealed that the refractile specks are composed of raised granules on the surface of the BioCoat™ Osteologic™ discs (FIG. 4C). Higher magnification analysis demonstrated single and compound granules on the discs with a shallow absorbed zone among compound granules (FIG. 4D). These results prompted us to extend the incubation time from 3 weeks to 7 weeks and to include cells on the discs for SEM analysis (i.e., no removal of cells by bleach). As a control, M-CSF/RANKL-differentiated monocytes on the osteologic discs are shown with one osteoclast and two absorption zones (FIG. 4E). In contrast, LL-37-differentiated monocytes exhibit raised granules on the discs with inclusion of granular material within the cells (FIG. 4F-H). The identification of the granules as minealrized material was verified by positive von Kossa staining (FIG. 5). These results demonstrate that LL-37-differentiated monocytes are bone-forming cells, distinct from in vitro derived bone absorbing osteoclasts.

Monoosteophils have Bone-Forming Ability In Vivo.

The capacity of the monoosteophils to form ectopic bone when transplanted with hydroxyapatite/tricalcium phosphate (HA/TCP) ceramic particles subcutaneously in NOD/SCID mice was examined. Histologic analysis of hematoxylin and eosin (H&E) sections representing 7 week old transplants showed that monoosteophil implants did not stain red for bone matrix-like structures as observed for MSC implants (Isenmann et al. 2009). An epiphyseal-like structure was observed only in the monoosteophil group but not in three control groups (monocytes alone, LL-37 alone, and blank control) (FIG. 12A-D). Epiphyseal-like structures are usually seen in the proliferating layer of growth plates in the histologic stages of long bone and epiphyseal development (Shapiro 2008; Kake et al. 2009). Masson trichrome staining showed that the epiphyseal-like structure contains collagen (blue color) (FIG. 12E-H). When the origin of the cellular material in the recovered implants was assessed using anti-human BSP II antibody, the interstitial tissue and cells within the epiphyseal-like structure were found to stain positive for anti-human BSP II, confirming their human origin (FIG. 12I-L). These results suggest that monoosteophils have the ability to form bone-like structures similar to the proliferating layer of growth plates Example 3

Monoosteophils are Distinct from Other Related Cell Types

Materials and Methods

The following the materials and methods were used in addition to those described in Examples 1 and 2 above:

Reagents. Recombinant human GM-CSF, M-CSF, IL-4, IFNα, and RANKL were purchased from ProSpec Tany TechnoGene Ltd (Rehovot 76124, Israel); LPS from *E. coli* (055:B5), Phalloidin, and saponin from Sigma-Aldrich (St. Louis, Mo., USA); anti-DC-SIGN PerCP/Cy5.5 (CD209, clone 9E9A8), anti-CD1a PE/Cy5 (Clone HI149), anti-CD90 PerCP/Cy5.5 (Clone 5E10), anti-CD163-PerCP/Cy5.5 (Clone GHI/61), anti-CD34 PerCP/Cy5.5 (Clone 4H11), and anti-MMP-9 (Clone F37P4A3) were purchased from Biolegend Inc (San Diego, Calif. 92121); anti-alkaline phosphatase (ALP, clone B4-78), anti-osteocalcin PE (OC, Clone 190125), anti-osteonectin (ON, Clone 122511), anti-RANKL (TRANCE, Clone 70525) and anti-RANK (Clone 80707), were purchased from R&D System (Minneapolis, Minn. 55413, USA); anti-bone sialoprotein II (BSPII, Clone ID1.2), anti-osteopontin (OP, clone AKm2A1), rabbit anti-human tartrate resistant acid phosphatase (TRAP) and anti-human cathepsin K (CK) polyclonal antibodies were from Santa Cruz Biotechnology Inc (Santa Cruz, Calif. 95060); anti-CD1b FITC (Clone MT101), anti-CD16-PerCP-Cy5.5 (Clone 3G8), anti-CD14-FITC (clone M5E2), isotype controls, and BioCoat™ Osteologic™ Discs were from BD Biosciences (Chicago, Ill., USA); anti-CD1c FITC (Clone AD5-8E7) was from Miltenyi Biotec Inc (Auburn, Calif. 95602) and anti-CD45 PE (clone HI30) was from eBiosciences (Dallas, Tex. 75312).

Monocyte preparation and differentiation. After isolation of monocytes as described in the examples above, monocytes were treated with serial dose of LL-37 (0.625 µM, 1.25 µM, 2.5 µM, 5 µM, or 10 µM) for differentiation for 3 days, 6 days, 14 days or more. After incubating for 6 days, cultures were fed every 2 days by removing half of the supernatant and adding fresh medium. For macrophage differentiation, monocytes were treated with medium only (Falzoni et al. 1995), with 100 ng/mL LPS (Palucka et al. 1999), 10 ng/mL GM-CSF (macrophage 1, Mϕ1), or 50 ng/mL M-CSF (macrophage 2, Mϕ2) for 6 days (Verreck et al. 2004). Monocyte-derived DCs were generated with 1,000 U/mL GM-CSF and 500 units/mL IL-4 (Verreck et al. 2004) or GM-CSF and 1000 U/mL IFNα (Tosello et al. 2009). Osteoclasts were differentiated from monocytes in the presence of RANKL and M-CSF (both at 25 ng/mL) (Sorensen et al. 2007).

Microscopic observation of differentiated monocytes. Monocytes were plated in culture media and treated with LL-37 (dose shown in the figures), LPS (100 ng/mL), GM-CSF (10 ng/mL), M-CSF (50 ng/mL), GM-CSF (1,000 U/mL)/IL-4 (500 units/mL), GM-CSF (1,000 U/mL)/IFNα (1,000 U/mL), or MCSF/RANKL (both at 25 ng/mL) and photographed with the Leica DMI 3000B (Leica Microsystems Inc, Bonnockburn, Ill. 60015) inverted microscope.

Phagocytosis. 6-day LL-37-, medium-, LPS-, GM-CSF-, and M-CSF-differentiated monocytes ($1 \times 10^6$/mL) in tissue culture medium supplemented with 10% FBS in a 24-well plate were mixed with fluorescent labeled latex beads at a multiplicity ratio of 1:500, and incubated for 1 hour at 37° C. After being washed three times, cells were analyzed using FACSCanton II and Flowjo software.

Cytokine multiplex analysis. Fresh monocytes were plated at $1 \times 10^6$ cells/mL in RPMI 1640 medium containing 10% FBS in 48-well plates and incubated with medium only, LL-37, LPS, GM-CSF, M-CSF, M-CSF/RANKL for 6 days, or/and 14 days and 21 days. Supernatant was collected and analyzed using the Human Cytokine 30-flex antibody bead kit from Biosource International Inc., including IL-1β, IL-1ra, IL-2, IL-2R, IL-4, IL-5, IL-6, IL-7, IL-8, IL-10, IL-12, IL-13, IL-15, IL-17, TNFα, IFNα, IFNγ, G-CSF, GM-CSF, MIP-1α, MIP-1β, MIG, RANTES, eotaxin, MCP-1, IP-10, VEGF, HGF, FGF-basic, and HGF. Cytokine concentrations were calculated using Bio-flex Manager 3.0 software with an eight-parameter, curve-fitting algorithm applied for standard curve calculations (Zhang et al. 2008b).

Figure 19:
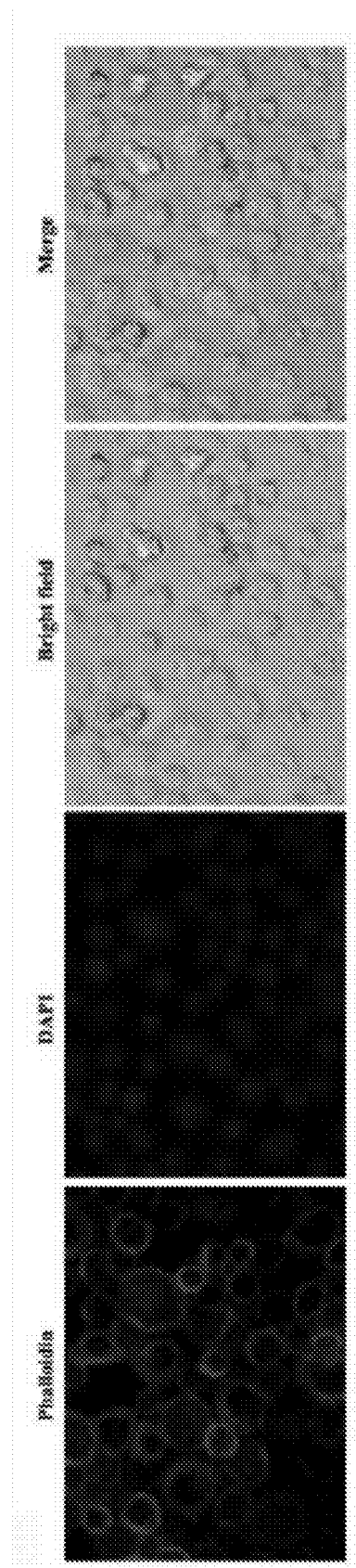
FIG. 19 shows exemplary images of cells that were incubated in the presence of 5 µM LL-37 for 6 days, fixed and permeabilized, then stained with phalloidin-Alexa 594 and DAPI and observed by a fluorescence microscope.
Figure 20:
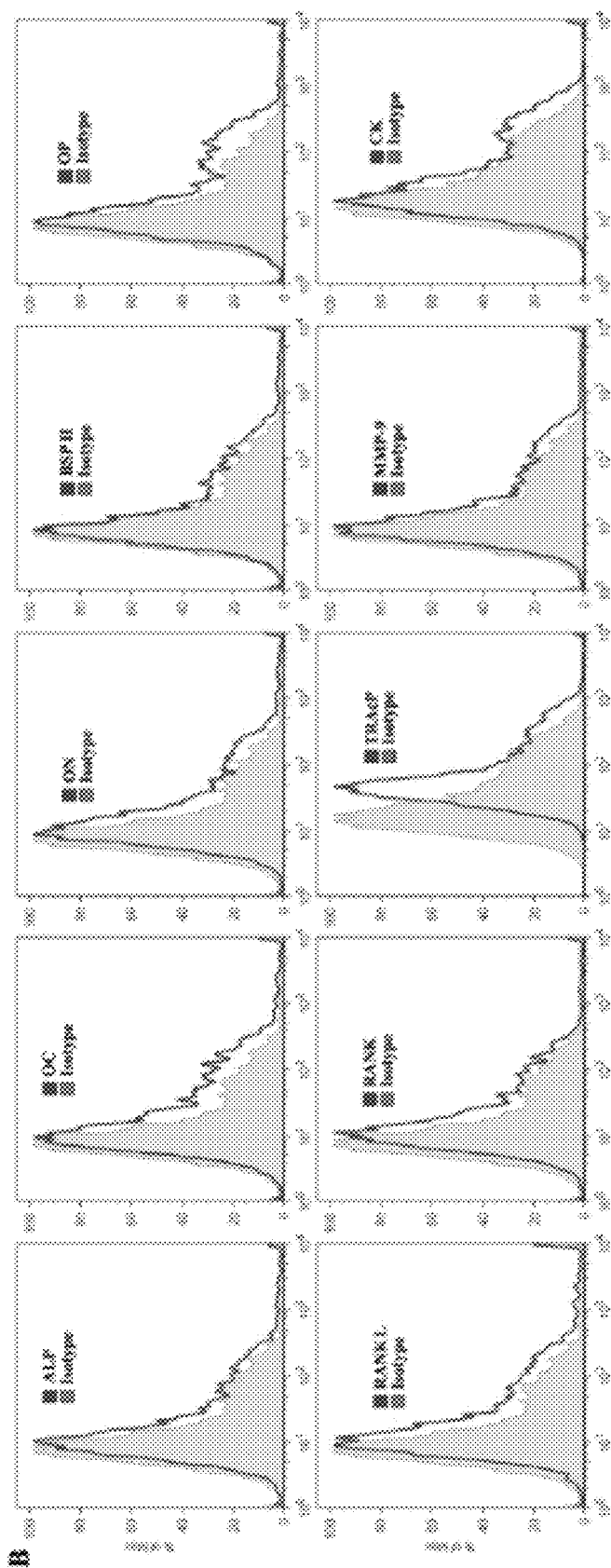
FIG. 20 shows monocytes that were incubated in the presence of 5 µM LL-37 for 6 days, then harvested, stained with antibodies (ALP, OC, ON, BSP II, OP, RANKL, RANK, TRAcP, MMP-9 and CK) and analyzed by flow cytometry to illustrate surface protein staining. Isotype control is shaded.
Figure 21:
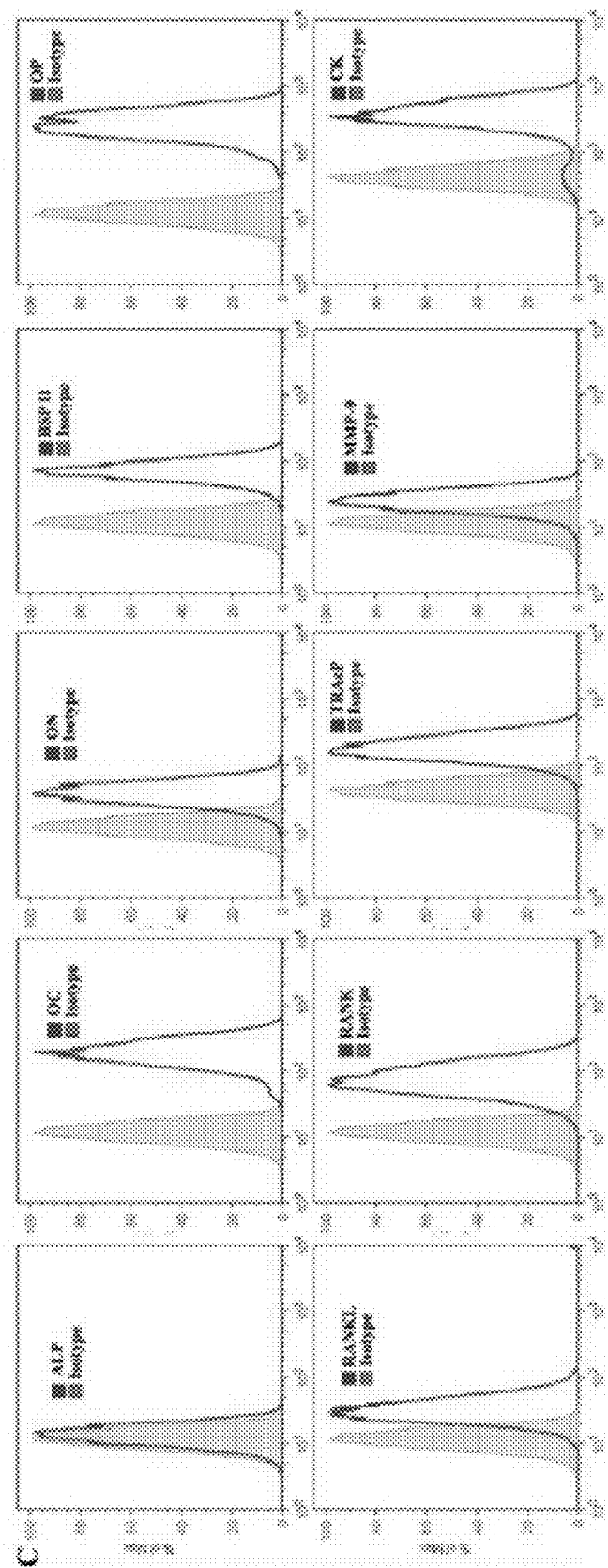
FIG. 21 shows monocytes that were incubated in the presence of 5 µM LL-37 for 6 days, harvested, fixed and permeabilized, stained with antibodies (ALP, OC, ON, BSP II, OP, RANKL, RANK, TRAcP, MMP-9 and CK) and analyzed by flow cytometry to illustrate intracellular protein staining. Data shown were from one of four independent experiments. Isotype control is shaded.

Monoosteophils are Distinct from Monocyte-Derived Osteoclasts and Mesenchymal Stem Cells in Morphology, Surface Markers, and/or Cytokine Release Additional studies were performed to fully characterize monoosteophil bone forming properties and to determine if their ability to use existing bone material to build new bone also means that they express markers of both osteoclast and osteoblast lineages. Phalloidin staining showed that after differentiation for 6 days, most monoosteophils are round, adherent cells with actin rings (FIG. 19)—similar to osteoclasts, but mononuclear. In addition, 6 day monoosteophils express a low level of TRAP, a marker normally expressed by bone resorbing osteoclasts and activated macrophages, on their cell surface (Hayman et al. 2000). However, 6 day monoosteophils do not express other surface markers of osteoclasts including RANK, MMP-9, and cathepsin K (CK) (FIG. 20). In comparison to osteoblast markers, they do not express surface alkaline phosphatase (ALP), OC, osteonectin (ON), BSP II, or osteopontin (OP) (FIG. 20). Intracellular staining results showed that 6-day monoosteophils do express most of the expected osteoblast and osteoclast proteins except ALP (FIG. 21), which is one of the most prominent markers of MSC-derived osteoblasts. Intracellular staining also reveals the presence of RANKL in LL-37 treated monocytes, suggesting that RANKL may be locally released by these cells. These data indicated that monoosteophils share the actin ring of the osteoclast, and express some marker proteins of the osteoclast and osteoblast but these marker proteins are localized to the cytoplasm and not to the cell surface.

Figure 6:
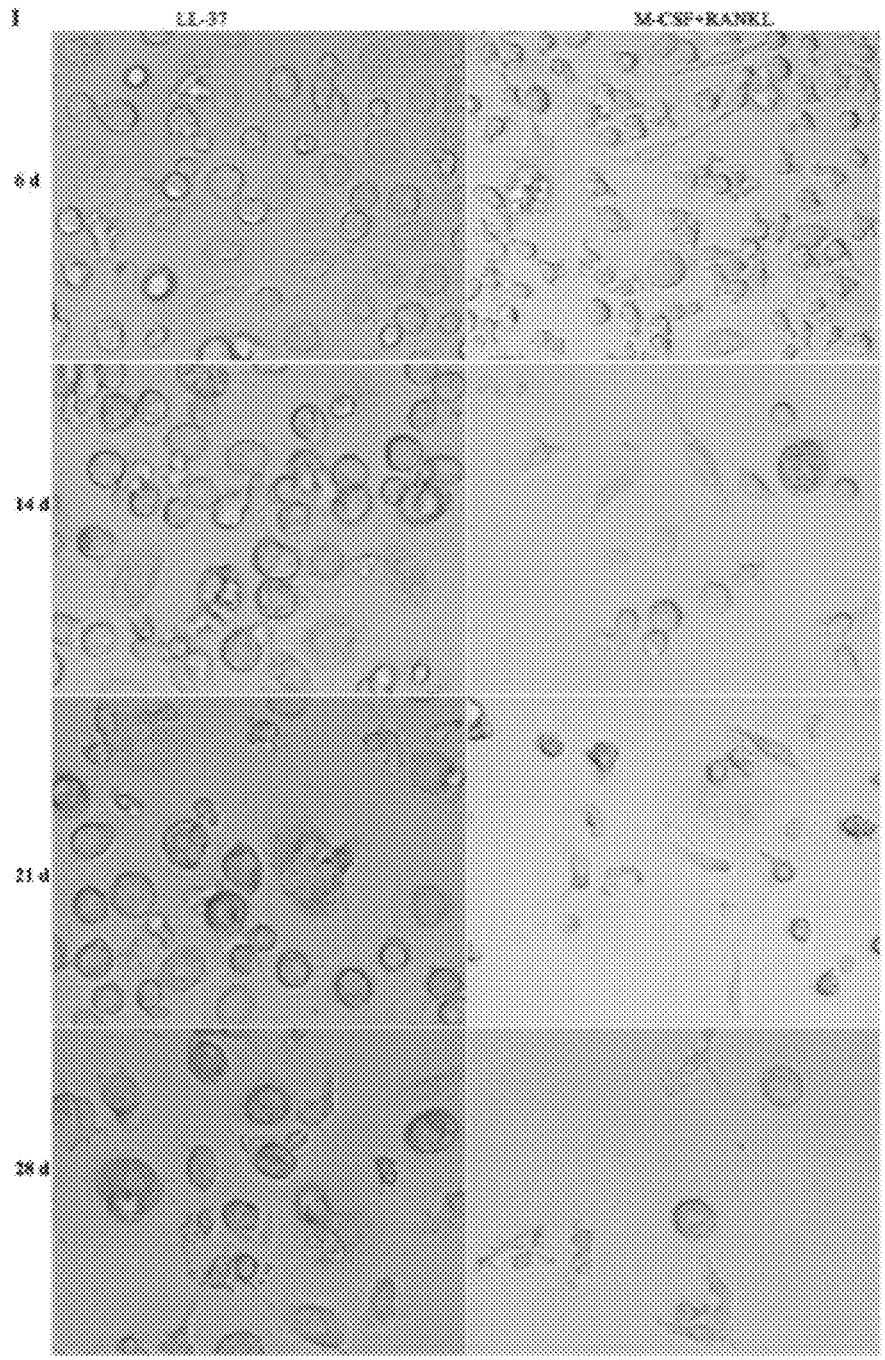
FIG. 6 shows exemplary phase contrast microscopy (magnification 200×) images illustrating cell morphology of monocytes seeded at a concentration of $1 \times 10^6$/mL treated with 5 µM LL-37 (left column) or 25 ng/mL of M-CSF/RANKL (right column) after 6 days, 14 days, 21 days or 28 days of incubation.
Figure 7:
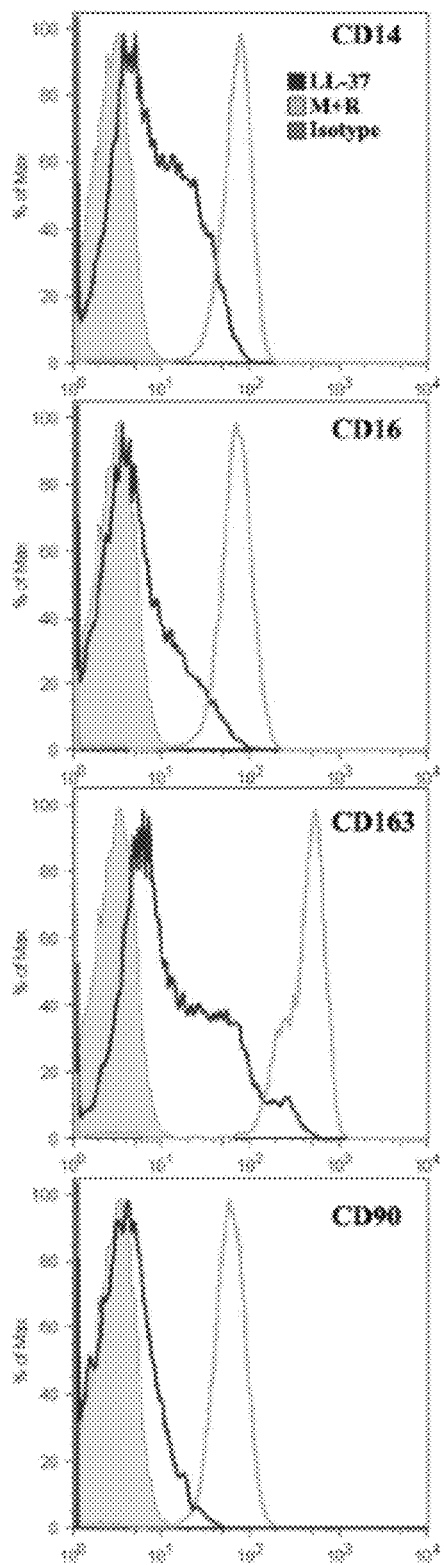
FIG. 7 shows flow cytometry results of differentiated monocytes that were seeded at a concentration of $1 \times 10^6$/mL incubated with LL-37 (dark traces) and M-CSF/RANKL (M+R; light traces) (at concentrations described in FIG. 4) or isotype control (shaded) for 6 days and stained with antibodies for CD14, CD16, CD163 and CD90.
Figure 8:
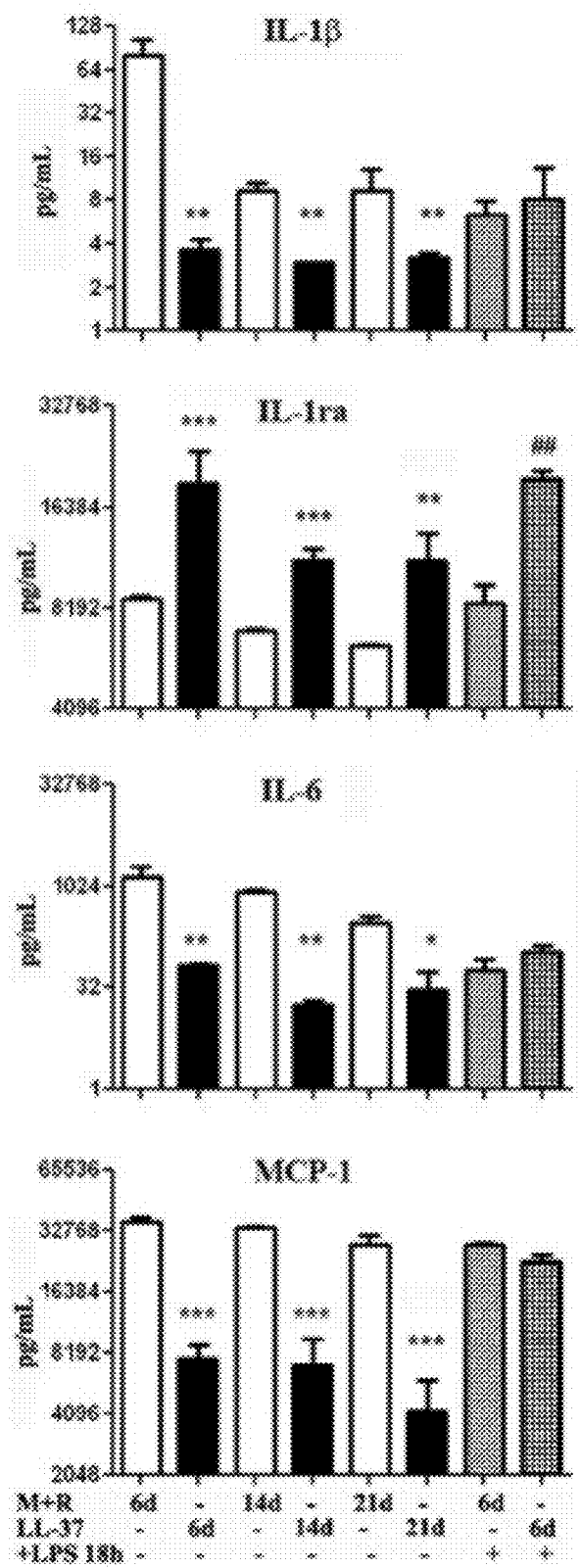
FIG. 8 is a series of bar graphs illustrating cytokine levels in the supernatant of LL-37- and MCSF/RANKL-differentiated monocytes (treated as described in FIG. 6) with or without LPS treatment. In the LPS treated experiment, 6-day LL-37- and M-CSF/RANKL-differentiated monocytes were collected, resuspended at the concentration of $1 \times 10^6$/mL, and incubated with 100 ng/mL LPS for 18 hours and cytokine levels were detected in the supernatant (mean±SE, n=3). Data represent three independent experiments performed. M+R: M-CSF+RANKL ($p<0.01$, *$p<0.001$ in comparison with M-CSF/RANKL-differentiated monocytes; ##$p<0.01$ in comparison with M-CSF/RANKL-differentiated monocytes treated with LPS for 18 hours).
Figure 9:
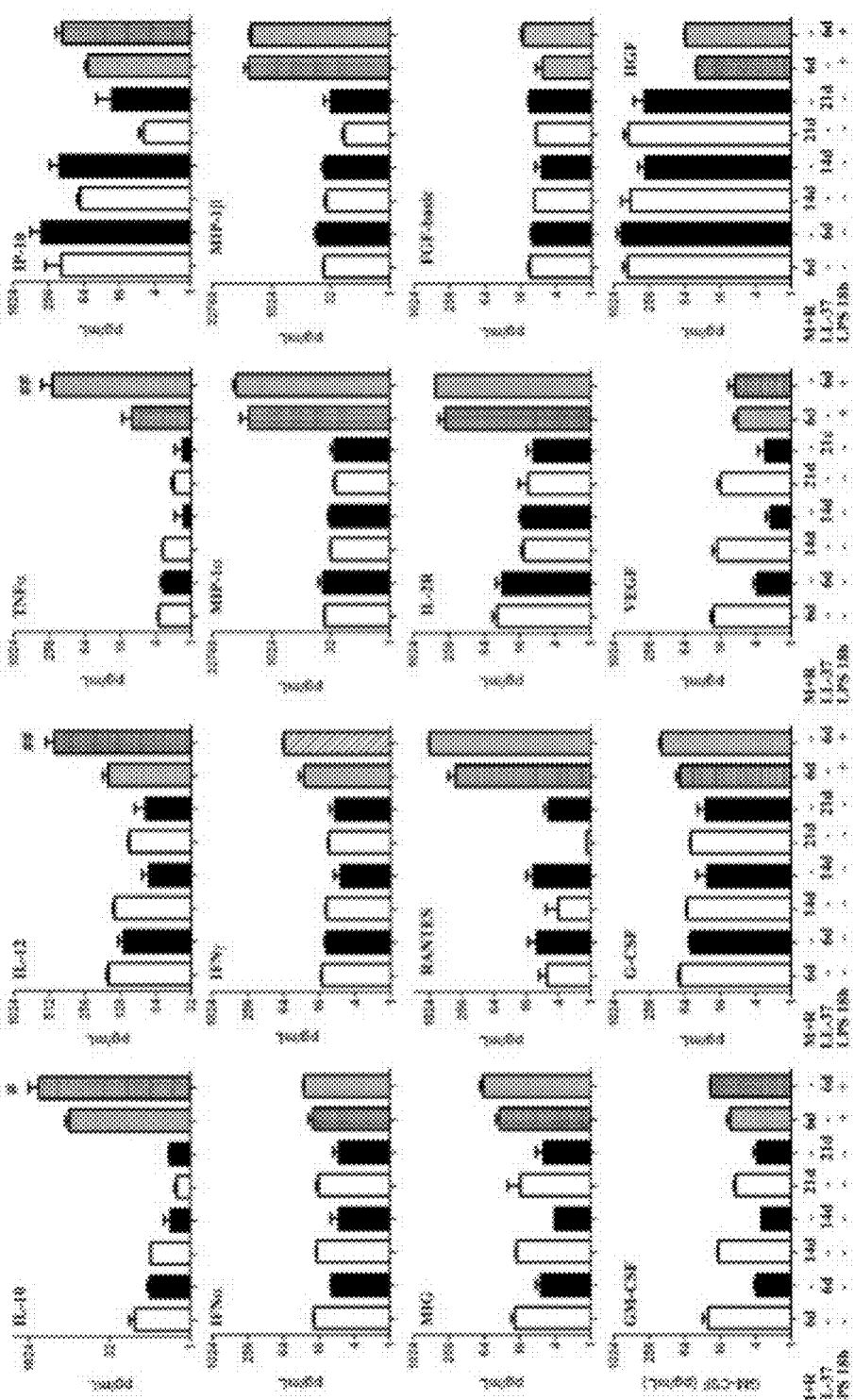
FIG. 9 is a series of bar graphs illustrating cytokine release between LL-37-differentiated monocytes and M-CSF/RANKL-differentiated osteoclasts. Monocytes were incubated in the presence of 5 µM LL-37 or M-CSF/RANKL (both at 25 ng/mL). Cytokine levels in the supernatant of LL-37- and M-CSF/RANKL-differentiated monocytes were evaluated using the Human Cytokine 30-flex antibody bead kit. In the experiment with LPS treatment, 6-day LL-37- or M-CSF/RANKL-differentiated monocytes were collected, resuspended at the concentration of $1 \times 10^6$/mL, and incubated with 100 ng/mL LPS for 18 hours. Cytokine levels were detected in the supernatant. Data (mean±SE) were from three independent experiments performed (##$p<0.01$ in comparison with M-CSF/RANKL (M+R)-differentiated monocytes treated with LPS for 18 hours).

Osteoclasts are large multinucleated cells arising through fusion of mononuclear hematopoietic stem cells found in the bone marrow, spleen, and peripheral blood, (Jilka et al. 1998; Rehman et al. 2003; Urbich et al. 2003; Schmeisser et al. 2001; Fernandez et al. 2000). The multinucleation characteristic of the osteoclast is the primary morphological feature that distinguishes an osteoclast from its precursor. Culture of unfractionated peripheral-blood monocytes with M-CSF and RANKL is sufficient to induce their differentiation in vitro to osteoclasts (Teitelbaum 2000). LL-37-differentiated monocytes were directly compared to monocyte-derived osteoclasts for morphology, survival, surface markers, and cytokine release. Results showed that although LL-37-differentiated cells are morphologically similar, they survive better than M-CSF/RANKL-derived osteoclasts after 28 days in terms of cell numbers (FIG. 6; movies not shown). While both treatments showed two adherent cell types, namely round large cells and irregular shaped cells at 28 days, a higher percentage of irregular shaped cells was observed in osteoclast differentiation medium compared to LL-37 differentiation medium at 6 days. Surface marker staining showed that 6-day MCSF/RANKL-treated monocytes expressed higher levels of CD14, CD163, CD16 and CD90 compared to 6-day LL-37-differentiated monocytes (FIG. 7). In addition, cytokine release analysis showed that 6-day LL-37-differentiated monocytes released lower levels of IL-1β, IL-6, MCP-1, but higher levels of IL-1ra than osteoclasts after differentiation for all time points analyzed (FIG. 8). Furthermore, 6-day LL-37-differentiated monocytes showed increased production of IL-1ra, IL-10, IL-12, IP-10, and GM-CSF than 6-day M-CSF/RANKL-differentiated monocytes in response to LPS (FIG. 8 and FIG. 9). The cytokine release profile in response to LPS suggests that LL-37-differentiated monocytes have an anti-inflammatory function. Thus, these data demonstrate that although LL37-differentiated cells share the morphology of giant cells similar to monocyte-derived osteoclasts, they have distinctive cell surface markers and cytokine release profiles.

Figure 10:
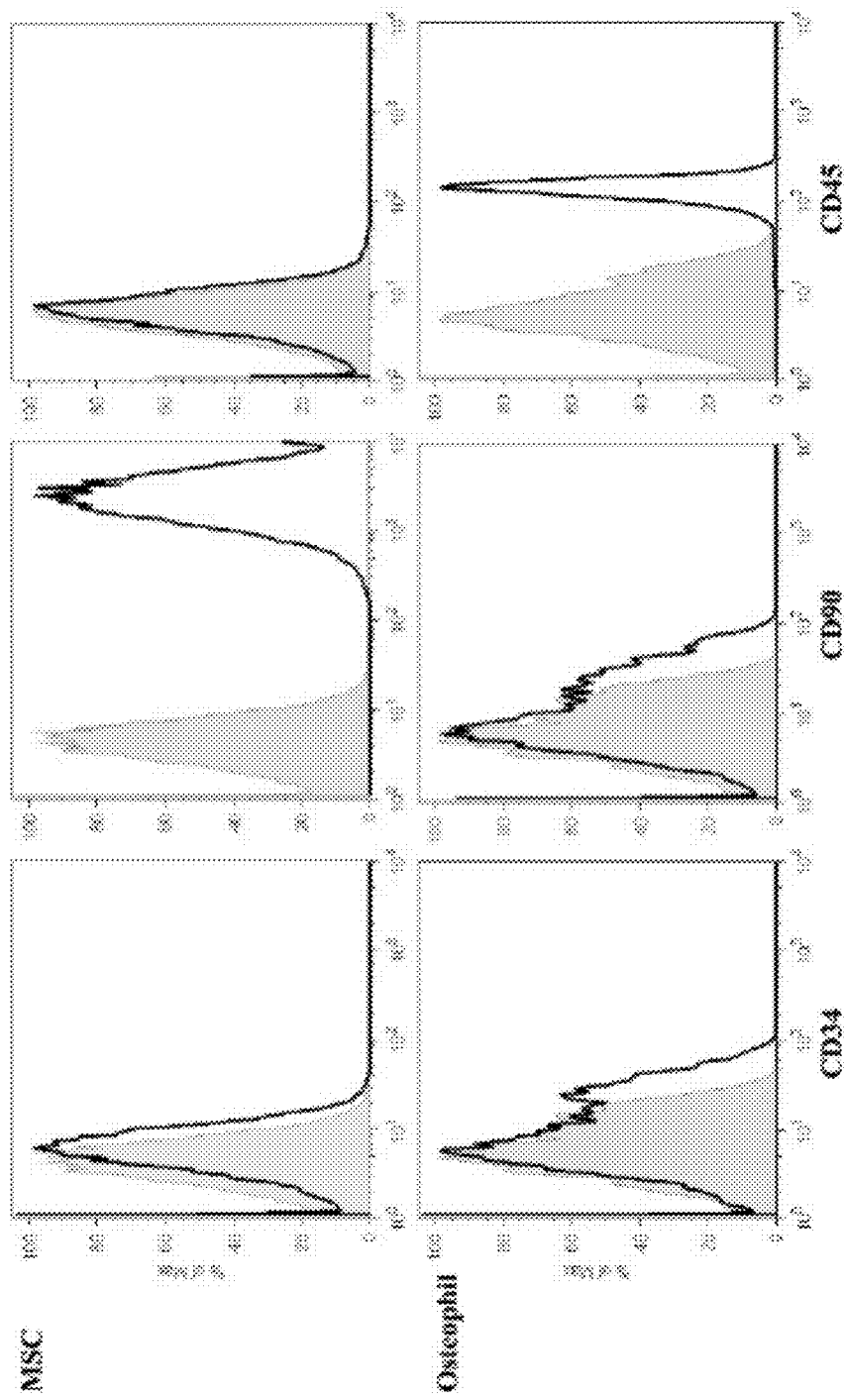
FIG. 10 shows that LL-37-differentiated monocytes express different surface markers (CD34, CD90 and CD45) than mesenchymal stem cells (MSCs). MSCs and 6-day 5 µM LL-37-differentiated monocytes (monoosteophils) were harvested, stained with antibodies, and analyzed by using flow cytometry and Flowjo software. Data represent one of three independent experiments performed. Isotype controls are shaded.
Figure 11:
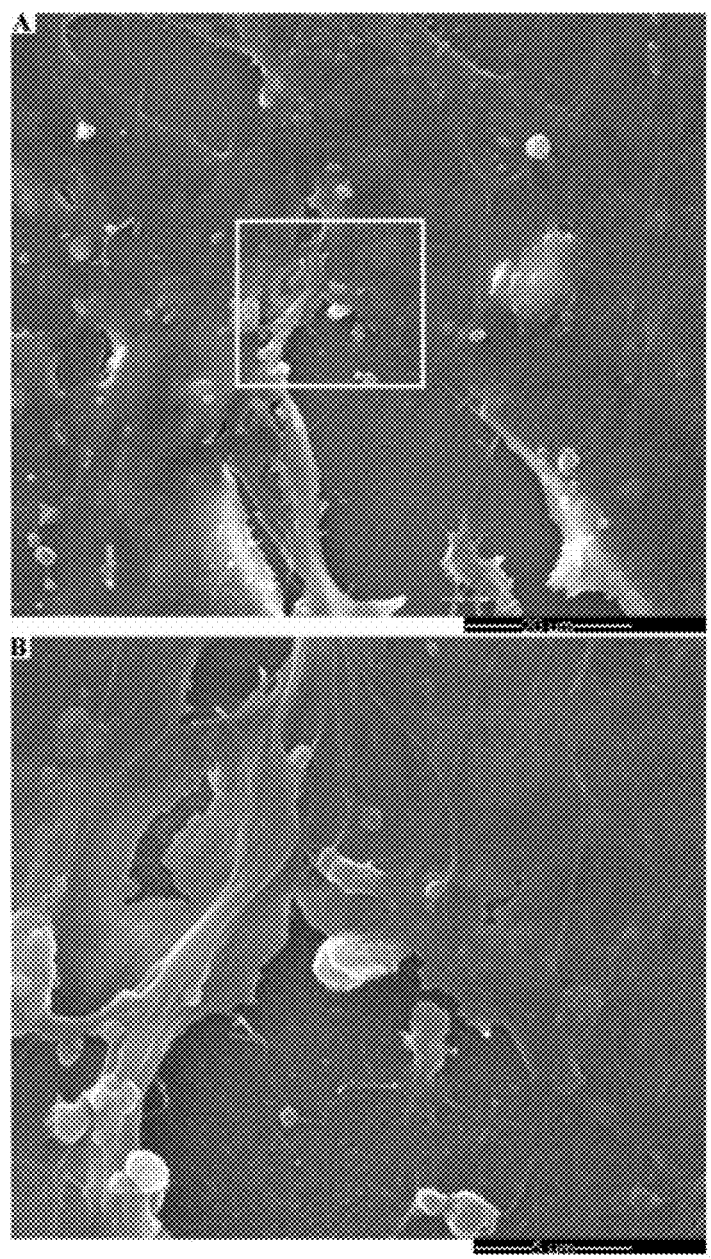
FIG. 11 illustrates differentiation of MSCs on an osteologic disc. MSCs were incubated in the α-MEM supplemented with 10% FCS, 100 µM L-ascorbate-2-phosphate, $10^{-7}$ M dexamethasone on BioCoat™ Osteologic™ Discs in 5% CO2 atmosphere. After incubation for 4 weeks, built-up structures and cells were shown using SEM (A-B).
Figure 12:
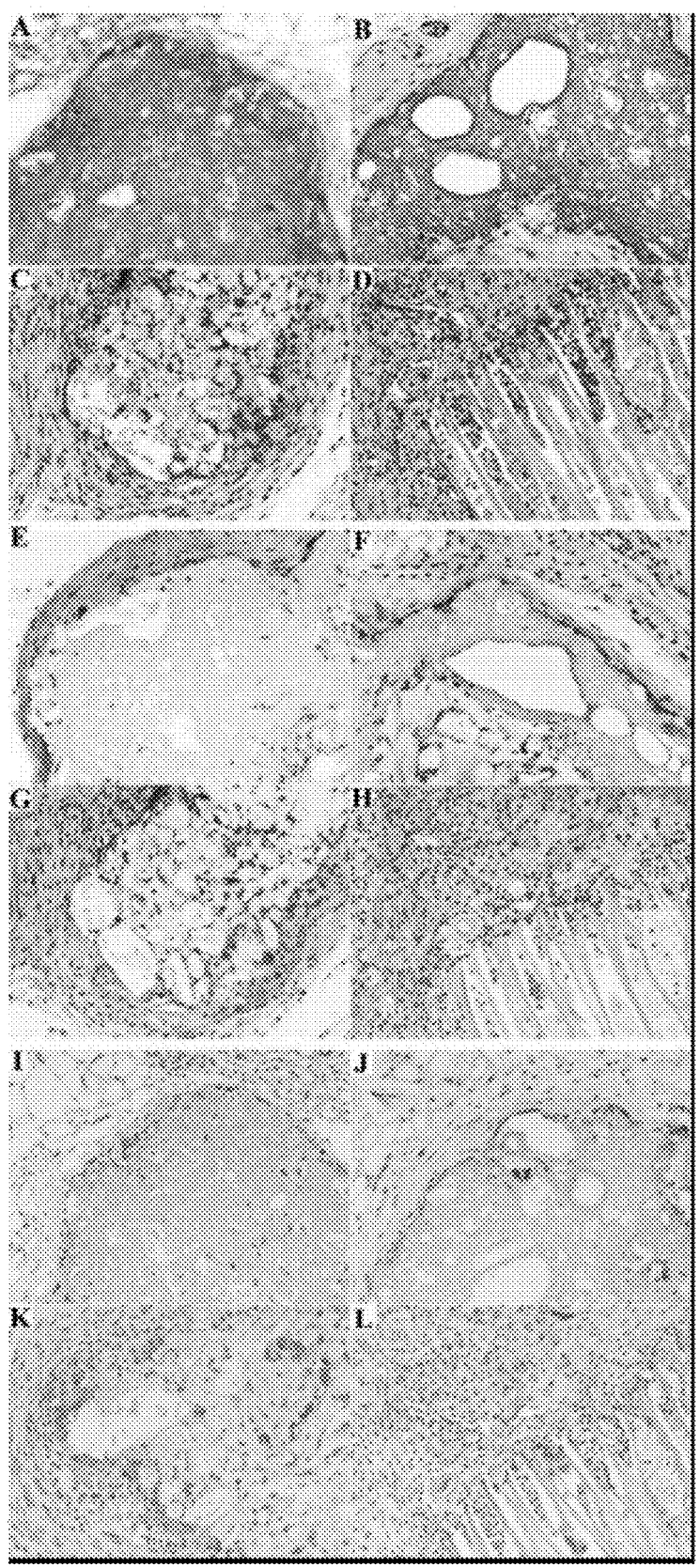
FIG. 12 shows exemplary photographs of bone-forming implants harvested from NOD/SCID mice implanted subcutaneously with hydroxyapatite/tricalcium phosphate only (A, E, I), with 5 µM LL-37 (B, F, J), with $5 \times 10^6$ monocytes (C, G, K), or 5 µM LL-37 plus $5 \times 10^6$ monocytes (D, H, L) after 7 weeks of treatment. The implants were stained with haematoxylin and eosin (A-D), masson trichrome (E-H), or anti-human BSP II antibody (I-L) (magnification 100×).

Because LL-37-differentiated monocytes were determined not to be true osteoclasts, it was determined whether LL-37-differentiated monocytes share properties with mesenchymal stem cells (MSCs), the precursors of osteoblasts. In the process of bone generation and repair, MSCs differentiate into osteoblasts and osteocytes. To answer this question, cell surface markers of both LL-37-differentiated monocytes and MSCs were compared. Neither MSCs nor LL-37-differentiated cells express the bone marrow stem cell marker CD34. However, while MSCs express CD90 (Thy1), a marker for a variety of stem cells, they do not express CD45, a common leukocyte marker. In contrast, LL-37-differentiated monocytes express CD45 but do not express CD90 (FIG. 10). Moreover, LL-37-differentiated monocytes exhibit both round enlarged and irregular cell shapes while MSC exhibit spindle shape morphology only (data not shown). Furthermore, when cultured under osteogenic inductive conditions on BioCoat™ Osteologic™ Discs, MSC exhibited a different pattern of bone formation compared with LL-37-differentiated monocytes as indicated by using SEM (FIG. 11). Thus, LL-37-differentiated monocytes, which are distinct from both osteoclasts and precursor of osteoblasts, are a distinctive type of bone forming cells. In addition to the three types of bone cells, osteoclast from M-CSF/RANKL-derived monocyte, osteoblast from MSC, and osteocyte from MSC-derived osteoblast, LL-37-differentiated monocytes are now a fourth type. The name "monoosteophil" is used to distinguish them from the three other types of bone cells and to emphasize their relation to monocytes.

Monoosteophils are Distinct from In Vitro Differentiated Macrophages and Dendritic Cells.

Circulating monocytes have the capacity to differentiate into a variety of phagocytes, including macrophages, dendritic cells (DCs), osteoclasts, microglia in the central nervous system, and Kupffer cells in the liver (Gordon 1995; Miyamoto et al. 2001; Servet-Delprat et al. 2002; Naito et al. 1997). To investigate these possible lineages, LL-37-differentiated monocytes were first compared to monocyte-derived macrophages. Thus, it was important to compare monoosteophils to monocyte-derived macrophage and DC lineages. At least 4 methods have been used to generate macrophages from monocytes, including incubation with medium only (Falzoni et al. 1995), LPS (Palucka et al. 1999), GM-CSF to produce Mφ1, or M-CSF to produce Mφ2 (Verreck et al. 2004).

Figure 13:
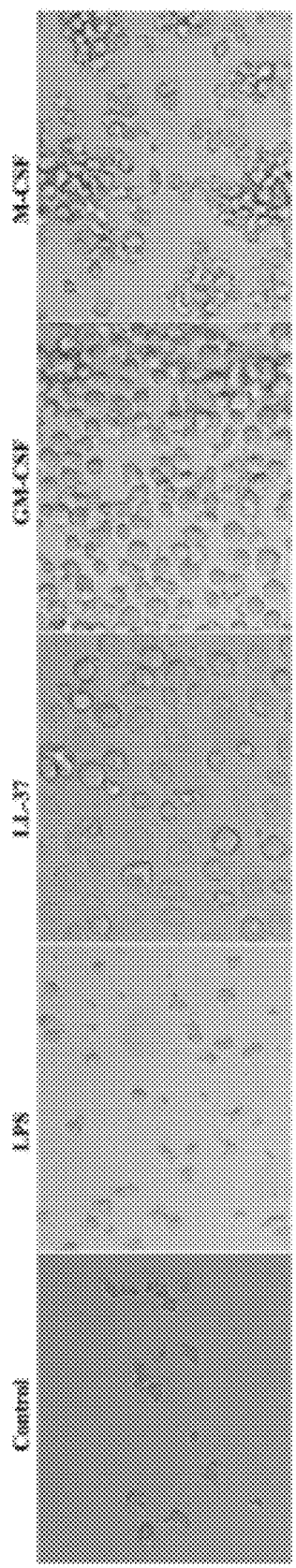
FIG. 13 shows exemplary phase contrast microscopy images to show cell morphology (magnification of 200×) of negatively isolated monocytes seeded at the concentration of $1 \times 10^6$/mL and incubated in the presence or absence (control) of 100 ng/mL LPS, 5 µM LL-37, 10 ng/mL GM-CSF, or 50 ng/mL M-CSF for 6 days.
Figure 14:
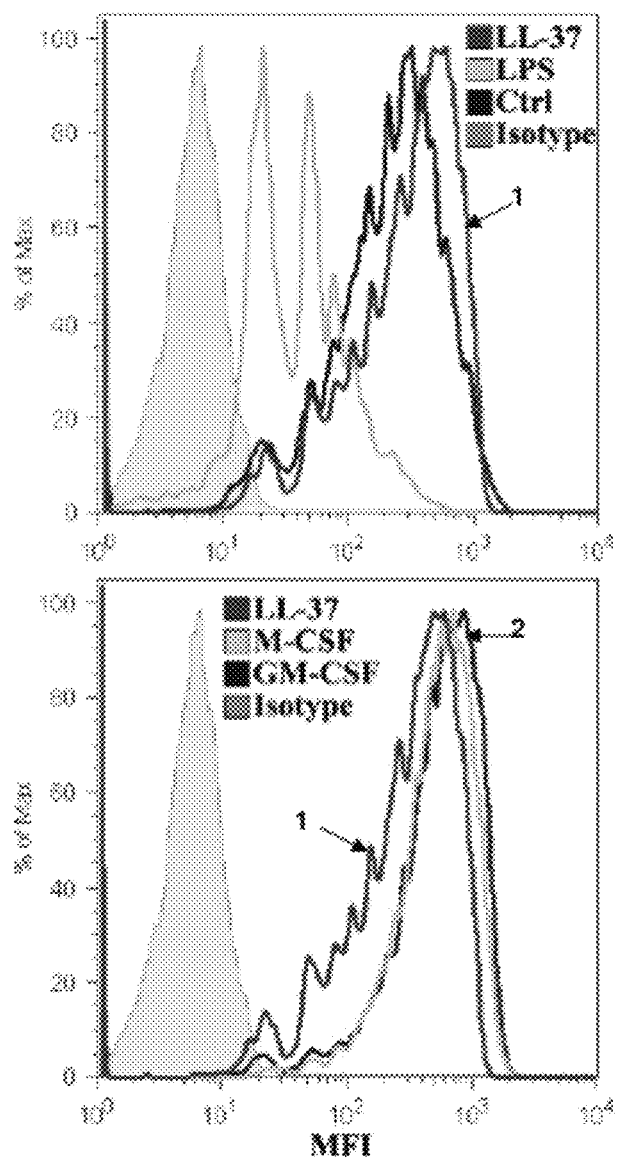
FIG. 14 shows flow cytometry results that illustrate phagocytosis of medium-(control), LPS (top, light trace), LL-37 (top and bottom, dark trace 1), GM-CSF (bottom, dark trace 2), or M-CSF (bottom, light trace) differentiated monocytes (after 6 days at concentrations described in FIG. 12) seeded at a concentration of $1 \times 10^6$/mL mixed with fluorescent labeled latex beads at a multiplicity ratio of 1:500 (MFI, mean fluorescence intensity) and incubated at 37° C. for 1 hour. Isotype control is shaded.
Figure 15:
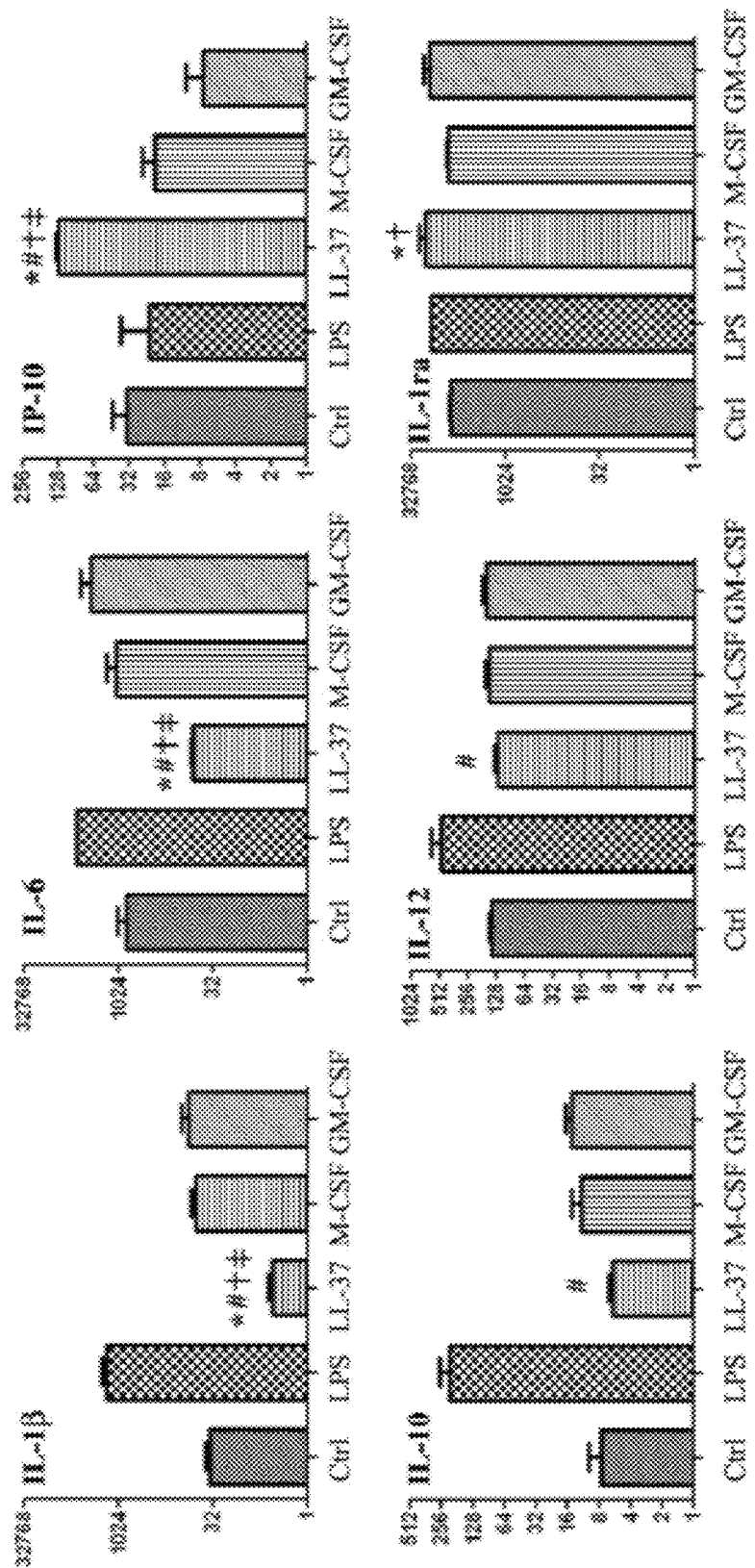
FIG. 15 is a series of bar graphs illustrating cytokine levels in the cultured supernatant of monocytes seeded at $1 \times 10^6$/mL that were incubated with medium (control), LPS, LL-37, GM-CSF, and M-CSF for 6 days at concentrations described in FIG. 12 (pg/mL, mean±SE).
Figure 16:
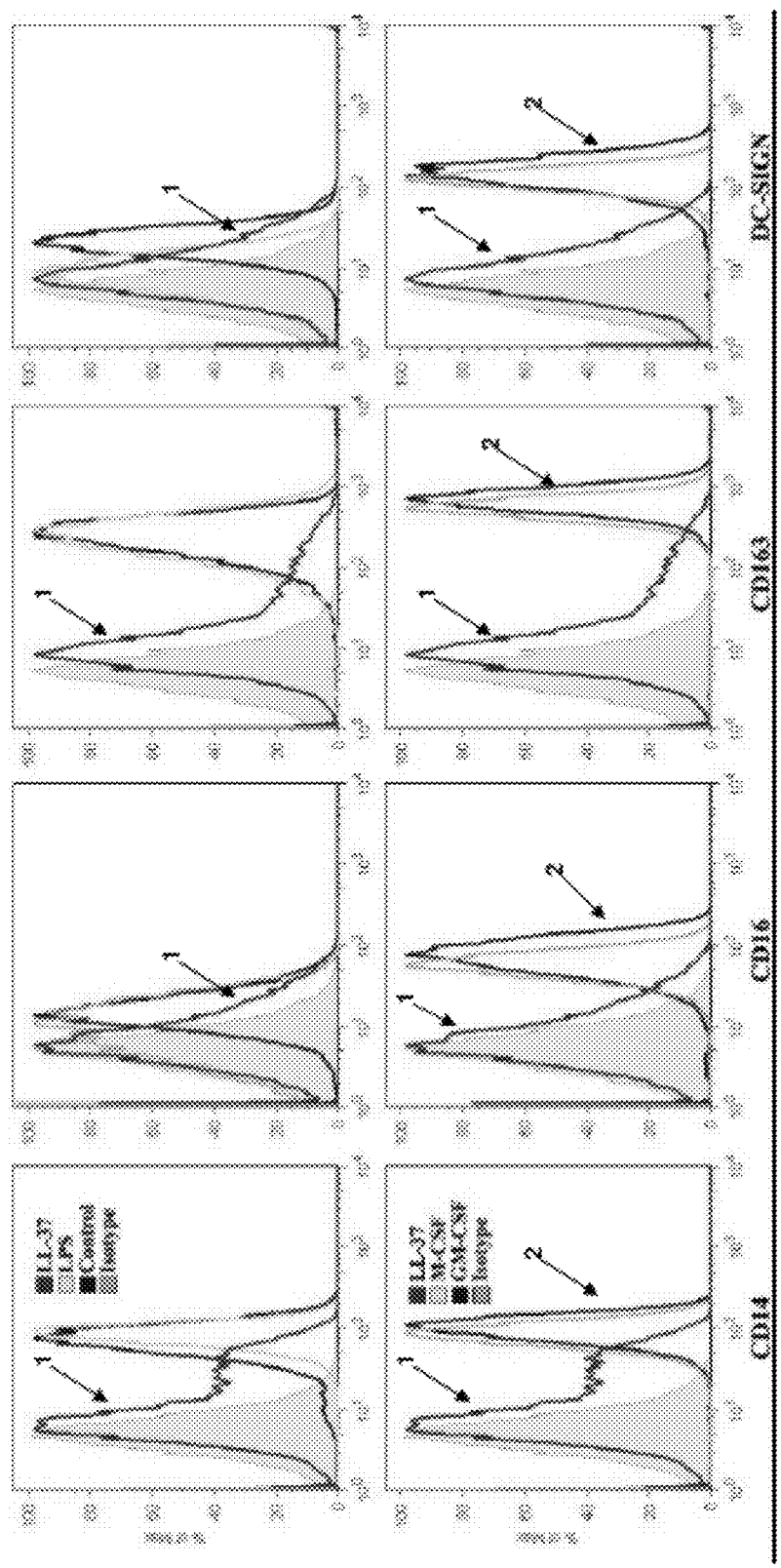
FIG. 16 shows flow cytometry results of monocytes seeded at 1×10⁶/mL that were incubated with medium (control), LPS (top, light traces), LL-37 (top and bottom, dark traces 1), GM-CSF (bottom, dark traces 2), or M-CSF (bottom, light traces) for 6 days at concentrations described in FIG. 12 and stained for CD14, CD16, CD163, and DC-SIGN. Data shown were from four independent experiments. Isotype control is shaded.

As shown in FIG. 13, the morphology of LL-37-differentiated cells at 6 days is distinct from monocytes treated with medium, LPS, GM-CSF or M-CSF. Further, a phagocytosis assay showed that the LL-37-differentiated cells retain their phagocytic function similar to the other generated macrophages except LPS-generated macrophage (FIG. 14). Cytokine profiles from the supernatants of 6-day LL-37 treated monocytes showed that LL-37-differentiated monocytes produce significantly less IL-1β and IL-6 and increased IP-10 in comparison with macrophages generated by the other methods (FIG. 15 and Table 1). Importantly, LL-37-differentiated monocytes release the highest levels of IL-1ra, the natural antagonist of IL-1β, and the lowest level of IL-1β compared to the other macrophage lineages. This suggests that LL-37-differentiated monocytes do not function as inflammatory cells, at least according to inflammatory cytokine release, a result similar to the previous report that LL-37 induces IL-1ra release from neutrophils (Zhang et al. 2008a). Moreover, cell surface marker staining showed that LL-37-differentiated monocytes expressed lower levels of CD163, DC-SIGN, and CD14 (FIG. 16) in comparison with the other macrophage lineages. Thus, although LL-37-differentiated monocytes retain theft phagocytic ability, they are distinct from other in vitro generated macrophages in terms of cell morphology, cytokine release, and cell surface markers.

Figure 17:
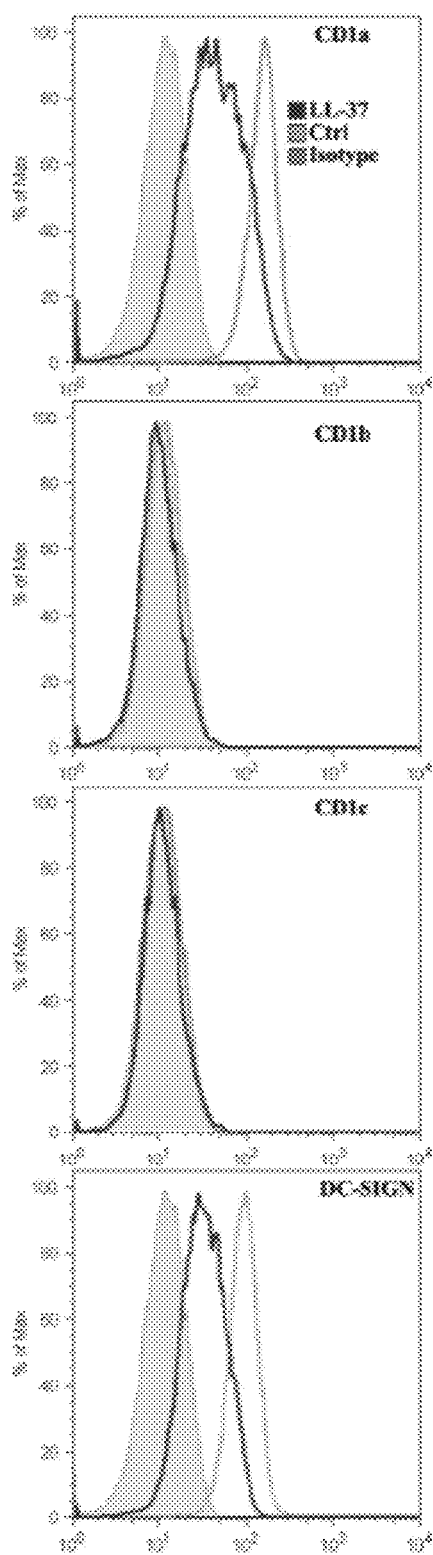
FIG. 17 shows flow cytometry results of LL-37-differentiated, negatively isolated monocytes seeded at a concentration of 1×10⁶/mL and treated with or without 5 µM LL-37 for 6 days and stained with antibodies (CD1a, CD1b, CD1c and DC-SIGN). Isotype control is shaded.
Figure 18:
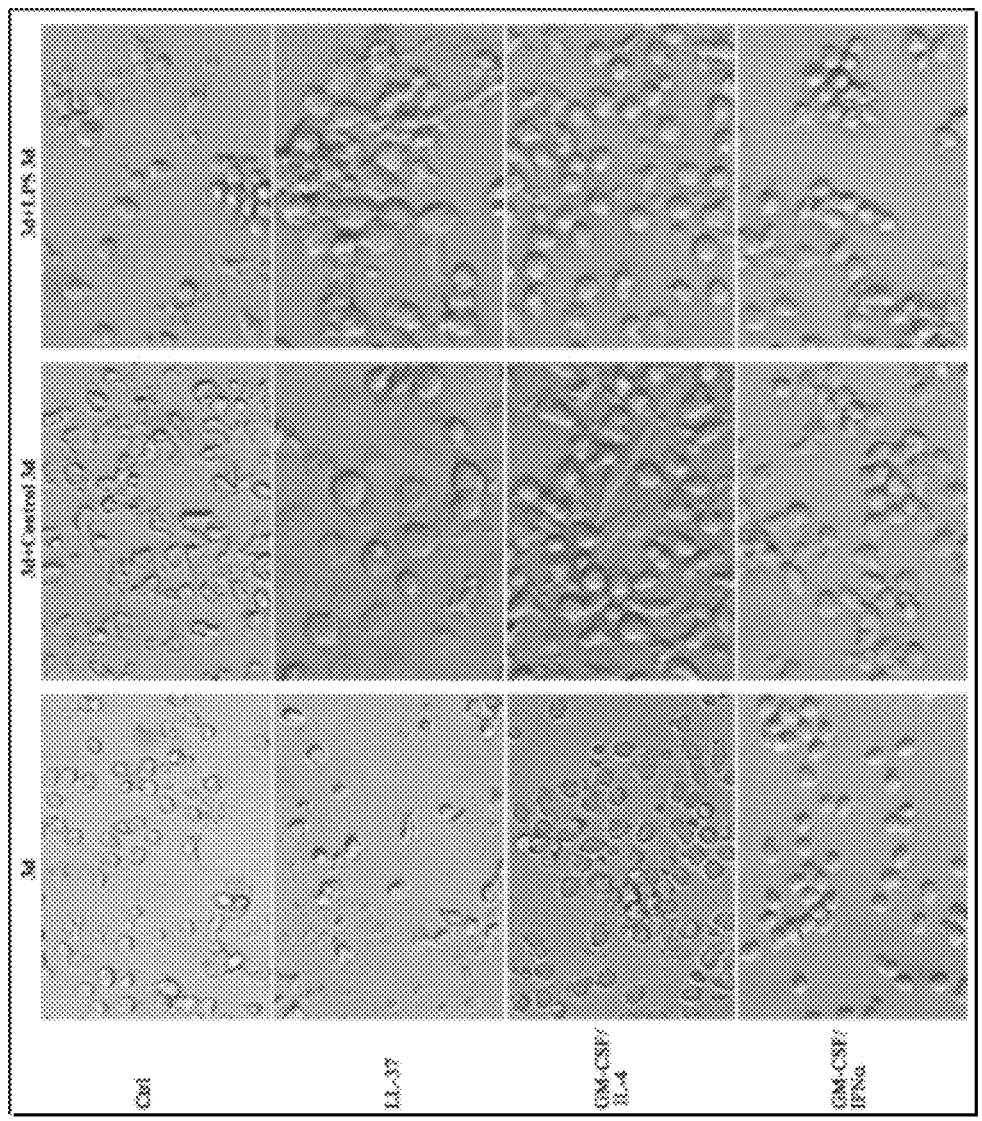
FIG. 18 shows exemplary phase contrast microscopy (magnification 200×) images illustrating cell morphology of monocytes seeded at a concentration of 1×10⁶/mL and treated with medium alone (control), 5 µM LL-37, (1,000 U/mL GM-CSF)+(500 U/mL IL-4), GM-CSF/IFNα (both at 1,000 U/mL) in the presence or absence of LPS treatment. Images shown were from one of four independent experiments.

Besides the differentiation of monocytes along the macrophage pathway, monocytes can also differentiate into DCs when cultured in the presence of GM-CSF and IL-4 (Sallusto & Lanzavecchia 1994; Romani et al. 1996 or GM-CSF and IFNα (Tosello et al. 2009). DCs are key players of adaptive immunity, unique in their ability to activate naïve T lymphocytes by operating as professional antigen-presenting cells (APC) to trigger a primary immune response. DCs are classified as immature prior to stimulation with agents such as LPS and as mature DCs after treatment with LPS, at which point they exhibit dendritic morphology (Zhou et al. 1996; Puig-Kroger et al. 2000). To investigate their interrelationships, LL-37-differentiated monocytes were compared to in vitro prepared DCs. As shown in FIG. 17. LL-37-differentiated monocytes express lower levels of CD1a and DC-SIGN than untreated controls and do not express CD1b and CD1c, typical markers of DCs (Sallusto & Lanzavecchia 1994). The morphology of LL-37-differentiated monocytes is distinct from GM-CSF/IL-4- and GM-CSF/IFNα-derived immature DCs in culture for 3 or 6 days. After incubation with LPS for 3 days, GM-CSF/IL-4- and GM-CSF/IFNα-derived immature DCs showed mature dendritic morphology, which is not observed for LL-37-differentiated cells or untreated cells (FIG. 18). These results demonstrate that monoosteophils do not share the characteristics of monocyte-derived DCs regarding cell surface markers and cell morphology.

REFERENCES

The references cited below and all references cited within the specification above are hereby incorporated by reference as if fully set forth herein.

Agerberth B, Charo J, Werr J, Olsson B, Idali F, et al. (2000) The human antimicrobial and chemotactic peptides LL-37 and alpha-defensins are expressed by specific lymphocyte and monocyte populations. Blood 96: 3086-3093.

Bandholtz L, Ekman G J, Vilhelmsson M, Buentke E, Agerberth B, et al. (2006) Antimicrobial peptide LL-37 internalized by immature human dendritic cells alters their phenotype. Scand J Immunol 63: 410-419.

TABLE 1

Comparison of cytokine release of LL-37-differentiated cells for 6 days with medium, LPS, GM-CSF, and M-CSF differentiated macrophages (Mean ± SEM)

|  | Control | LPS | LL-37 | GM-CSF | M-CSF |
| --- | --- | --- | --- | --- | --- |
| IL-4 | 9.0 ± 0.68 | 15.22 ± 0.13 | 7.16 ± 0.59 | 11.82 ± 0.98 | 11.07 ± 0.95 |
| IL-7 | 18.19 ± 3.21 | 41.82 ± 2.56 | 11.93 ± 1.96#†‡ | 26.89 ± 0.16 | 24.83 ± 1.68 |
| IFN-α | 12.40 ± 1.78 | 16.19 ± 1.17 | 9.93 ± 0.14 | 14.33 ± 1.27 | 19.83 ± 1.19 |
| IFN-γ | 13.47 ± 0.69 | 15.94 ± 0.49 | 12.13 ± 0.88 | 13.5 ± 0.47 | 14.67 ± 1.06 |
| GM-CSF | 18.97 ± 3.89 | 63.36 ± 0.30 | 3.96 ± 0.30*#‡ |  | 25.2 ± 5.51 |
| MIP-1α | 51.56 ± 2.41 | 238.46 ± 29.41 | 53.17 ± 12.97# | 72.20 ± 6.18 | 41.62 ± 2.63 |
| MIP-1β | 72.00 ± 12.12 | 427.82 ± 105.77 | 72.41 ± 9.86# | 70.42 ± 19.71 | 47.26 ± 1.46 |
| MIG | 18.14 ± 1.34 | 27.58 ± 0.93 | 7.16 ± 1.31*#†‡ | 17.21 ± 1.30 | 15.39 ± 2.01 |
| RANTES | 7.46 ± 2.79 | 10.88 ± 0.95 | 10.24 ± 3.87 | 5.42 ± 1.85 | 10.19 ± 1.38 |
| MCP-1 | 15463.5 ± 6862.6 | 9883.0 ± 4145.9 | 7720.3 ± 972.2‡ | 15362.1 ± 7902.6 | 34236.5 ± 1606.8 |
| IL-2R | 24.30 ± 1.62 | 140.27 ± 24.74 | 32.38 ± 7.04# | 47.16 ± 1.23 | 44.62 ± 4.89 |
| VEGF | 8.67 ± 0.87 | 61.16 ± 12.70 | 3.88 ± 0.41*#†‡ | 15.88 ± 2.99 | 22.12 ± 1.39 |
| G-CSF | 65.67 ± 4.51 | 1217.43 ± 81.09 | 51.79 ± 3.38# | 74.85 ± 2.60 | 75.71 ± 5.78 |
| HGF | 324.15 ± 35.68 | 52.40 ± 7.74 | 772.94 ± 126.71# | 505.18 ± 118.32 | 664.33 ± 112.85 |
| FGF-Basic | 9.95 ± 0.17 | 15.15 ± 0.75 | 10.28 ± 0.66 | 10.85 ± 0.22 | 11.54 ± 0.31 |

*$p < 0.05$ in comparison with medium-macrophages;
$p < 0.05$ vs LPS-macrophages;
†$p < 0.05$ vs GM-CSF-macrophages;
‡$p < 0.05$ vs M-CSF-macrophages.

Davidson D J, Currie A J, Reid G S, Bowdish D M, MacDonald K L, et al. (2004) The cationic antimicrobial peptide LL-37 modulates dendritic cell differentiation and dendritic cell-induced T cell polarization. J Immunol 172: 1146-1156.

De Y, Chen Q, Schmidt A P, Anderson G M, Wang J M, et al. (2000) LL-37, the neutrophil granule- and epithelial cell-derived cathelicidin, utilizes formyl peptide receptor-like 1 (FPRL1) as a receptor to chemoattract human peripheral blood neutrophils, monocytes, and T cells. J Exp Med 192: 1069-1074.

Ducy P, Schinke T, Karsenty G (2000) The osteoblast: a sophisticated fibroblast under central surveillance. Science 289: 1501-1504.

Falzoni S, Munerati M, Ferrari D, Spisani S, Moretti S, et al. (1995) The purinergic P2Z receptor of human macrophage cells. Characterization and possible physiological role. J Clin Invest 95: 1207-1216.

Fernandez Pujol B, Lucibello F C, Gehling U M, Lindemann K, Weidner N, et al. (2000) Endothelial-like cells derived from human CD14 positive monocytes. Differentiation 65: 287-300.

Franc N C, Dimarcq J L, Lagueux M, Hoffmann J, Ezekowitz R A (1996) Croquemort, a novel *Drosophila* hemocyte/macrophage receptor that recognizes apoptotic cells. Immunity 4: 431-443.

Frohm M, Gunne H, Bergman A C, Agerberth B, Bergman T, et al. (1996) Biochemical and antibacterial analysis of human wound and blister fluid. Eur J Biochem 237: 86-92.

Geissmann F, Jung S, Littman D R (2003) Blood monocytes consist of two principal subsets with distinct migratory properties. Immunity 19: 71-82.

Gordon S (1995) The macrophage. Bioessays 17: 977-986.

Hayman A R, Bune A J, Bradley J R, Rashbass J, Cox T M (2000) Osteoclastic tartrateresistant acid phosphatase (Acp 5): its localization to dendritic cells and diverse murine tissues. J Histochem Cytochem 48: 219-228.

Heilborn J D, Nilsson M F, Kratz G, Weber G, Sorensen O, et al. (2003) The cathelicidin anti-microbial peptide LL-37 is involved in re-epithelialization of human skin wounds and is lacking in chronic ulcer epithelium. J Invest Dermatol 120: 379-389.

Isenmann S, Arthur A, Zannettino A C, Turner J L, Shi S, et al. (2009) TWIST family of basic helix-loop-helix transcription factors mediate human mesenchymal stem cell growth and commitment. Stem Cells 27: 2457-2468.

Jilka R L, Weinstein R S, Bellido T, Parfitt A M, Manolagas S C (1998) Osteoblast programmed cell death (apoptosis): modulation by growth factors and cytokines. J Bone Miner Res 13: 793-802.

Johansson J, Gudmundsson G H, Rottenberg M E, Berndt K D, Agerberth B (1998) Conformation-dependent antibacterial activity of the naturally occurring human peptide LL-37. J Biol Chem 273: 3718-3724.

Kake T, Kitamura H, Adachi Y, Yoshioka T, Watanabe T, et al. (2009) Chronically elevated plasma C-type natriuretic peptide level stimulates skeletal growth in transgenic mice. Am J Physiol Endocrinol Metab 297: E1339-1348.

Kandler K, Shaykhiev R, Kleemann P, Klescz F, Lohoff M, et al. (2006) The antimicrobial peptide LL-37 inhibits the activation of dendritic cells by TLR ligands. Int Immunol 18: 1729-1736.

Khosla S, Westendorf J J, Oursler M J (2008) Building bone to reverse osteoporosis and repair fractures. J Clin Invest 118: 421-428.

Koczulla R, von Degenfeld G, Kupatt C, Krotz F, Zahler S, et al. (2003) An angiogenic role for the human peptide antibiotic LL-37/hCAP-18. J Clin Invest 111: 1665-1672.

Kuwana M, Okazaki Y, Kodama H, Izumi K, Yasuoka H, et al. (2003) Human circulating CD14+ monocytes as a source of progenitors that exhibit mesenchymal cell differentiation. J Leukoc Biol 74: 833-845.

Lacey D L, Timms E, Tan H L, Kelley M J, Dunstan C R, et al. (1998) Osteoprotegerin ligand is a cytokine that regulates osteoclast differentiation and activation. Cell 93: 165-176.

Malm J, Sorensen O, Persson T, Frohm-Nilsson M, Johansson B, et al. (2000) The human cationic antimicrobial protein (hCAP-18) is expressed in the epithelium of human epididymis, is present in seminal plasma at high concentrations, and is attached to spermatozoa. Infect Immun 68: 4297-4302.

Manolagas S C (2000) Birth and death of bone cells: basic regulatory mechanisms and implications for the pathogenesis and treatment of osteoporosis. Endocr Rev 21:115-137.

Miyamoto T, Ohneda O, Arai F, Iwamoto K, Okada S, et al. (2001) Bifurcation of osteoclasts and dendritic cells from common progenitors. Blood 98: 2544-2554.

Naito M, Hasegawa G, Takahashi K (1997) Development, differentiation, and maturation of Kupffer cells. Microsc Res Tech 39: 350-364.

Niyonsaba F, Iwabuchi K, Someya A, Hirata M, Matsuda H, et al. (2002) A cathelicidin family of human antibacterial peptide LL-37 induces mast cell chemotaxis. Immunology 106: 20-26.

Nuttall M E, Gimble J M (2004) Controlling the balance between osteoblastogenesis and adipogenesis and the consequent therapeutic implications. Curr Opin Pharmacol 4: 290-294.

Ong P Y, Ohtake T, Brandt C, Strickland I, Boguniewicz M, et al. (2002) Endogenous antimicrobial peptides and skin infections in atopic dermatitis. N Engl J Med 347:1151-1160.

Palucka K A, Taquet N, Sanchez-Chapuis F, Gluckman J C (1999) Lipopolysaccharide can block the potential of monocytes to differentiate into dendritic cells. J Leukoc Biol 65: 232-240.

Puig-Kroger A, Sanz-Rodriguez F, Longo N, Sanchez-Mateos P, Botella L, et al. (2000) Maturation-dependent expression and function of the CD49d integrin on monocyte-derived human dendritic cells. J Immunol 165: 4338-4345.

Randolph G J, Inaba K, Robbiani D F, Steinman R M, Muller W A (1999) Differentiation of phagocytic monocytes into lymph node dendritic cells in vivo. Immunity 11: 753-761.

Rehman J, Li J, Orschell C M, March K L (2003) Peripheral blood "endothelial progenitor cells" are derived from monocyte/macrophages and secrete angiogenic growth factors. Circulation 107: 1164-1169.

Romani N, Reider D, Heuer M, Ebner S, Kampgen E, et al. (1996) Generation of mature dendritic cells from human blood. An improved method with special regard to clinical applicability. J Immunol Methods 196: 137-151.

Sallusto F, Lanzavecchia A (1994) Efficient presentation of soluble antigen by cultured human dendritic cells is maintained by granulocyte/macrophage colonystimulating factor plus interleukin 4 and downregulated by tumor necrosis factor alpha. J Exp Med 179: 1109-1118.

Schaller-Bals S, Schulze A, Bals R (2002) Increased levels of antimicrobial peptides in tracheal aspirates of newborn infants during infection. Am J Respir Crit Care Med 165: 992-995.

Schmeisser A, Garlichs C D, Zhang H, Eskafi S, Graffy C, et al. (2001) Monocytes coexpress endothelial and macrophagocytic lineage markers and form cord-like structures in Matrigel under angiogenic conditions. Cardiovasc Res 49: 671-680.

Scott M G, Davidson D J, Gold M R, Bowdish D, Hancock R E (2002) The human antimicrobial peptide LL-37 is a multifunctional modulator of innate immune responses. J Immunol 169: 3883-3891.

Servet-Delprat C, Arnaud S, Jurdic P, Nataf S, Grasset M F, et al. (2002) Flt3+ macrophage precursors commit sequentially to osteoclasts, dendritic cells and microglia. BMC Immunol 3: 15.

Shapiro F (2008) Bone development and its relation to fracture repair. The role of mesenchymal osteoblasts and surface osteoblasts. Eur Cell Mater 15: 53-76.

Singhatanadgit, W., Salih, V., and Olsen, I. 2006. Up-regulation of bone morphogenetic protein receptor IB by growth factors enhances BMP-2-induced human bone cell functions. *J Cell Physiol* 209:912-922.

Sorensen O, Arnljots K, Cowland J B, Bainton D F, Borregaard N (1997) The human antibacterial cathelicidin, hCAP-18, is synthesized in myelocytes and metamyelocytes and localized to specific granules in neutrophils. Blood 90: 2796-2803.

Sorensen O, Bratt T, Johnsen A H, Madsen M T, Borregaard N (1999) The human antibacterial cathelicidin, hCAP-18, is bound to lipoproteins in plasma. J Biol Chem. pp. 22445-22451.

Sorensen O E, Follin P, Johnsen A H, Calafat J, Tjabring a G S, et al. (2001) Human cathelicidin, hCAP-18, is processed to the antimicrobial peptide LL-37 by extracellular cleavage with proteinase 3. Blood 97: 3951-3959.

Sorensen O E, Cowland J B, Theilgaard-Monch K, Liu L, Ganz T, et al. (2003) Wound healing and expression of antimicrobial peptides/polypeptides in human keratinocytes, a consequence of common growth factors. J Immunol 170: 5583-5589.

Sorensen M G, Henriksen K, Schaller S, Henriksen D B, Nielsen F C, et al. (2007) Characterization of osteoclasts derived from CD14+ monocytes isolated from peripheral blood. J Bone Miner Metab 25: 36-45.

Teitelbaum S L (2000) Bone resorption by osteoclasts. Science 289: 1504-1508.

Teitelbaum S L, Ross F P (2003) Genetic regulation of osteoclast development and function. Nat Rev Genet 4: 638-649.

Tjabring a GS, Aarbiou J, Ninaber D K, Drijfhout J W, Sorensen O E, et al. (2003) The antimicrobial peptide LL-37 activates innate immunity at the airway epithelial surface by transactivation of the epidermal growth factor receptor. J Immunol 171: 6690-6696.

Tosello V, Zamarchi R, Merlo A, Gorza M, Piovan E, et al. (2009) Differential expression of constitutive and inducible proteasome subunits in human monocytederived DC differentiated in the presence of IFN-alpha or IL-4. Eur J Immunol 39: 56-66.

Urbich C, Heeschen C, Aicher A, Dernbach E, Zeiher A M, et al. (2003) Relevance of monocytic features for neovascularization capacity of circulating endothelial progenitor cells. Circulation 108: 2511-2516.

van der Does A M, Beekhuizen H, Ravensbergen B, Vos T, Ottenhoff T H, et al. LL-37 directs macrophage differentiation toward macrophages with a proinflammatory signature. J Immunol 185: 1442-1449.

Verreck F A, de Boer T, Langenberg D M, Hoeve M A, Kramer M, et al. (2004) Human IL-23-producing type 1 macrophages promote but IL-10-producing type 2 macrophages subvert immunity to (myco)bacteria. Proc Natl Acad Sci USA 101:4560-4565.

Waskow C, Liu K, Darrasse-Jeze G, Guermonprez P, Ginhoux F, et al. (2008) The receptor tyrosine kinase Flt3 is required for dendritic cell development in peripheral lymphoid tissues. Nat Immunol 9: 676-683.

Yu, Y., Yang, J. L., Chapman-Sheath, P. J., and Walsh, W. R. 2002. TGF-beta, BMPS, and their signal transducing mediators, Smads, in rat fracture healing. *J Biomed Mater Res* 60:392-397.

Yuasa K, Mori K, Ishikawa H, Sudo A, Uchida A, et al. (2007) Characterization of two types of osteoclasts from human peripheral blood monocytes. Biochem Biophys Res Commun 356: 354-360.

Zhao Y, Glesne D, Huberman E (2003) A human peripheral blood monocyte-derived subset acts as pluripotent stem cells. Proc Natl Acad Sci USA 100: 2426-2431.

Zhang Z, Chernyholmes G, Chang F, Rose D M, Schraufstatter I, et al. (2009) Evidence that cathelicidin peptide LL-37 may act as a functional ligand for CXCR2 on human neutrophils. Eur J Immunol 39: 3181-3194.

Zhang Z, Chernyholmes G, Shively J E (2008a) Neutrophil secondary necrosis is induced by LL-37 derived from cathelicidin. J Leukoc Biol 84: 780-788.

Zhang Z, Chernyholmes G, Mao A, Marek C, Longmate J, et al. (2008b) High plasma levels of MCP-1 and eotaxin provide evidence for an immunological basis of fibromyalgia. Exp Biol Med (Maywood) 233: 1171-1180.

Zhou L J, Tedder T F (1996) CD14+ blood monocytes can differentiate into functionally mature CD83+ dendritic cells. Proc Natl Acad Sci USA 93: 2588-2592.

What is claimed is:

1. A method of producing a population of monocyte-derived bone-forming cells, the method comprising:
    isolating a population of monocytes from a blood sample from a subject;
    and
    culturing the isolated monocytes in the presence of an effective dose of LL-37 until they differentiate into the population of monocyte-derived bone-forming cells.

2. The method of claim 1, wherein the effective dose of LL-37 is between about 1.25 µM and 10 µM.

3. The method of claim 1, wherein the effective dose of LL-37 is 5 µM.

4. The method of claim 1, wherein the blood sample is obtained from a subject in need of bone repair.

5. The method of claim 1, wherein the blood sample is obtained from a donor subject.

6. A monocyte derived bone-forming cell population produced by the method of claim 1.

7. The monocyte-derived bone-forming cell population of claim 6, wherein the cell population expresses osteocalcin (OC), osteonectin (ON), bone sialoprotein II (BSP II), osteopontin (OP), RANK, RANKL, MMP-9, tartrate resistant acid phosphatase (TRAP), and cathepsin K (CK).

8. The monocyte-derived bone-forming cell population of claim 6, wherein the effective dose of LL-37 is between about 1.25 µM and 10 µM.

9. The monocyte-derived bone-forming cell population of claim 6, wherein the effective dose of LL-37 is about 5 µM.

* * * * *

UNITED STATES PATENT AND TRADEMARK OFFICE
CERTIFICATE OF CORRECTION

| | | |
|---|---|---|
| PATENT NO. | : 8,513,013 B2 | Page 1 of 1 |
| APPLICATION NO. | : 13/249877 | |
| DATED | : August 20, 2013 | |
| INVENTOR(S) | : Zhifang Zhang et al. | |

It is certified that error appears in the above-identified patent and that said Letters Patent is hereby corrected as shown below:

In the Specification

Statement Regarding Federally Sponsored Research section, Column 1, Lines 15-18, please delete:
"The invention was made with Government support under Grant No. CA84202 awarded by the National Institutes of Health (NIH). The Government has certain rights in the invention"

And insert:
--This invention was made with government support under CA084202 awarded by the National Institutes of Health. The government has certain rights in the invention.--

Signed and Sealed this
Eleventh Day of March, 2025

Coke Morgan Stewart
*Acting Director of the United States Patent and Trademark Office*